United States Patent
Pontzer et al.

(10) Patent No.: US 6,833,256 B1
(45) Date of Patent: Dec. 21, 2004

(54) INTERFERON TAU MUTANTS AND METHODS FOR MAKING THEM

(75) Inventors: Carol H. Pontzer, Silver Spring, MD (US); Lynnette H. Shorts, Silver Spring, MD (US); Christina Dancz Clark, Cambridge, MA (US)

(73) Assignee: University of Maryland, College Park, MD (US)

( * ) Notice: Subject to any disclaimer, the term of this patent is extended or adjusted under 35 U.S.C. 154(b) by 113 days.

(21) Appl. No.: 09/599,413

(22) Filed: Jun. 22, 2000

Related U.S. Application Data

(60) Provisional application No. 60/140,411, filed on Jun. 22, 1999.

(51) Int. Cl.$^7$ .................................. C12P 21/04
(52) U.S. Cl. .................... 435/69.7; 435/69.51; 530/351; 424/85.4; 424/85.7
(58) Field of Search .............................. 435/69.51, 440; 424/85.4, 85.7; 530/351

(56) References Cited

U.S. PATENT DOCUMENTS

| | | | |
|---|---|---|---|
| 5,705,363 A | | 1/1998 | Imakawa |
| 5,738,845 A | | 4/1998 | Imakawa |
| 5,939,286 A | | 8/1999 | Johnson et al. |
| 5,942,223 A | * | 8/1999 | Bazer ........................ 424/85.4 |
| 5,958,402 A | | 9/1999 | Bazer et al. |
| 6,060,450 A | | 5/2000 | Soos et al. |

FOREIGN PATENT DOCUMENTS

| | | | |
|---|---|---|---|
| WO | WO 94/10313 | | 5/1994 |
| WO | WO 97/33607 | | 9/1997 |
| WO | WO 97/39127 | | 10/1997 |
| WO | WO 09807863 | | 2/1998 |
| WO | WO 99/20653 | * | 4/1999 ........... C07K/14/56 |

OTHER PUBLICATIONS

Goeddel et al. Human leukocyte interferon produced by *E. coli* is biologically active. 1980. Nature. 287:411–416.*
Walter, M.R. Three–dimensional models of interferon–alpha subtypes IFN–con1, IFN–alpha8, and IFN–alpha derived from the crystal structure of IFN–alpha2b. 1997. Seminars in Oncology, 24(3 Suppl 9): S9–52–S9–62.*
Pontzer, C. et al. Potent Anti–Feline Immunodeficiency Virus and Anti–Human Immunotherapy Virus Effect of IFN–Tau. The Journal of Immunology, 1997, 158:4351–4357.
Li, J. et al. Structure–Function Relationships in the Interferon– Tau. The Journal of Biological Chemistry. Oct. 7, 1994, vol. 269, No. 40, pp. 24826–24833. U.S.A.
Radhakrishnan, R. et al. Crystal Structure of Ovine Interferon–Tau at 2.1 Angstrom Resolution. J. Mol. Biol. (1999) 286, pp. 151–162.
Goldman, L. et al, Mapping Human Interferon–Alpha Binding Determinants of the Type I Interferon Receptor Subunit IFNAR–1 with Human/Bovine IFNAR–1 Chimeras. Biochemistry 1998, 37, pp. 13003–13010.
Cheetham, B. et al. Structure–function Studies of Human Interferons–Tau: Enhanced Activity on Human and Murine Cells, Antiviral Research 15 (1991) pp. 27–40.
Alexenko, A. P., Ealy, A. D., and Roberts, R. M. (1999) J. Interferon Cytokine Res. 19, 1335–1341.
Subramaniam, P. S., Khan, S. A., Pontzer, C. H., and Johnson, H. M. (1995) Proc. Natl. Acad. Sci. U. S. A. 92, 12270–12274.
Pontzer, C. H., Yamamoto, J. K., Bazer, F. W., Ott, T. L., and Johnson, H. M. J. Immunol. 158, 4351–4357.
Soos, J. M., Subramaniam, P. S., Hobeika, A. C., Schiffenbauer, J. andJohnson, H. M. (1995) J. Immunol. 155, 2747–2753.
Pontzer, C. H., et al., J Interferon Research 14, 133–41 (1994).
Li, J. et al., J Biol Chemistry vol. 269: 40, 24826–24833 (1994).
Pontzer, C. H., Ott, T. L., Bazer, F. W., and Johnson, H. M. (1990) Proc. Natl. Acad. Sci. U. S. A. 87, 5945–5949.

* cited by examiner

*Primary Examiner*—Elizabeth Kemmerer
*Assistant Examiner*—Dong Jiang
(74) *Attorney, Agent, or Firm*—Foley & Lardner

(57) ABSTRACT

The present invention is directed to the field of animal and human health, and more particularly to pharmacological uses of analogs or mutants of interferon-tau (IFN-τ) that differ from native IFN-τ because of substitutions of amino acids near the amino terminus of the IFN-τ molecule that impart improved biological activity. The IFN-τ mutants described in this disclosure have low toxicity, retain the same or slightly reduced antiviral activity compared with highly effective IFN-alpha, and have enhanced antiproliferative activity compared to native IFN-tau, making them useful in treating viral infections, cancer, and immune system diseases including autoimmune diseases. The present invention is also directed to a method for making novel recombinant proteins, especially interferons, interleukins, and cytokines, polypeptide hormones and other biopharmaceuticals that have improved biological activity over known proteins and/or lower toxicity and/or increased stability.

12 Claims, No Drawings

SEQUENCE LISTING

<160> NUMBER OF SEQ ID NOS: 20

<210> SEQ ID NO 1
<211> LENGTH: 516
<212> TYPE: DNA
<213> ORGANISM: ovine

<400> SEQUENCE: 1

```
tgctacctgt cgcgaaaact gatgctggac gctcgagaaa atttaaaact gctggaccgt      60
atgaatcgat tgtctccgca cagctgcctg caagaccgga aagacttcgg tctgccgcag     120
gaaatggttg aaggtgacca actgcaaaaa gaccaagctt tcccggtact gtatgaaatg     180
ctgcagcagt ctttcaacct gttctacact gaacattctt cggccgcttg ggacactact     240
cttctagaac aactgtgcac tggtctgcaa cagcaactgg accatctgga cacttgccgt     300
```

```
ggccagggta tgggtgaaga agactctgaa ctgggtaaca tggatccgat cgttactgtt      360
aaaaaatatt tccagggtat ctacgactac ctgcaggaaa aaggttactc tgactgcgct      420
tgggaaatcg tacgcgttga aatgatgcgg gccctgactg tgtcgactac tctgcaaaaa      480
cggttaacta aatgggtgg tgacctgaat tctccg                                 516
```

```
<210> SEQ ID NO 2
<211> LENGTH: 172
<212> TYPE: PRT
<213> ORGANISM: ovine

<400> SEQUENCE: 2
```

Cys Tyr Leu Ser Arg Lys Leu Met Leu Asp Ala Arg Glu Asn Leu Lys
 1               5                  10                  15

Leu Leu Asp Arg Met Asn Arg Leu Ser Pro His Ser Cys Leu Gln Asp
             20                  25                  30

Arg Lys Asp Phe Gly Leu Pro Gln Glu Met Val Glu Gly Asp Gln Leu
         35                  40                  45

Gln Lys Asp Gln Ala Phe Pro Val Leu Tyr Glu Met Leu Gln Gln Ser
     50                  55                  60

Phe Asn Leu Phe Tyr Thr Glu His Ser Ser Ala Ala Trp Asp Thr Thr
 65                  70                  75                  80

Leu Leu Glu Gln Leu Cys Thr Gly Leu Gln Gln Gln Leu Asp His Leu
                 85                  90                  95

Asp Thr Cys Arg Gly Gln Gly Met Gly Glu Glu Asp Ser Glu Leu Gly
            100                 105                 110

Asn Met Asp Pro Ile Val Thr Val Lys Lys Tyr Phe Gln Gly Ile Tyr
            115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170

```
<210> SEQ ID NO 3
<211> LENGTH: 188
<212> TYPE: PRT
<213> ORGANISM: Homo sapiens

<400> SEQUENCE: 3
```

Met Ala Leu Thr Phe Ala Leu Leu Val Ala Leu Leu Val Leu Ser Cys
 1               5                  10                  15

Lys Ser Ser Cys Ser Val Gly Cys Asp Leu Pro Gln Thr His Ser Leu
             20                  25                  30

Gly Ser Arg Arg Thr Leu Met Leu Leu Ala Gln Met Arg Lys Ile Ser
         35                  40                  45

Leu Phe Ser Cys Leu Lys Asp Arg His Asp Phe Gly Phe Pro Gln Glu
     50                  55                  60

Glu Phe Gly Asn Gln Phe Gln Lys Ala Glu Thr Ile Pro Val Leu His
 65                  70                  75                  80

Glu Met Ile Gln Gln Ile Phe Asn Leu Phe Ser Thr Lys Asp Ser Ser
                 85                  90                  95

Ala Ala Trp Asp Glu Thr Leu Leu Asp Lys Phe Tyr Thr Glu Leu Tyr
            100                 105                 110

```
Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 4
<211> LENGTH: 172
<212> TYPE: PRT
<213> ORGANISM: ovine

<400> SEQUENCE: 4

Cys Tyr Leu Ser Arg Lys Leu Met Leu Asp Ala Arg Arg Asn Leu Lys
  1               5                  10                  15

Leu Leu Asp Arg Met Asn Arg Leu Ser Pro His Ser Cys Leu Gln Asp
                20                  25                  30

Arg Lys Asp Phe Gly Leu Pro Gln Glu Met Val Glu Gly Asp Gln Leu
            35                  40                  45

Gln Lys Asp Gln Ala Phe Pro Val Leu Tyr Glu Met Leu Gln Gln Ser
        50                  55                  60

Phe Asn Leu Phe Tyr Thr Glu His Ser Ser Ala Ala Trp Asp Thr Thr
 65                  70                  75                  80

Leu Leu Glu Gln Leu Cys Thr Gly Leu Gln Gln Gln Leu Asp His Leu
                85                  90                  95

Asp Thr Cys Arg Gly Gln Gly Met Gly Glu Glu Asp Ser Glu Leu Gly
                100                 105                 110

Asn Met Asp Pro Ile Val Thr Val Lys Lys Tyr Phe Gln Gly Ile Tyr
            115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170

<210> SEQ ID NO 5
<211> LENGTH: 172
<212> TYPE: PRT
<213> ORGANISM: ovine

<400> SEQUENCE: 5

Cys Tyr Leu Ser Arg Lys Leu Met Leu Asp Ala Arg Glu Asn Leu Met
  1               5                  10                  15

Leu Leu Asp Arg Met Asn Arg Leu Ser Pro His Ser Cys Leu Gln Asp
                20                  25                  30

Arg Lys Asp Phe Gly Leu Pro Gln Glu Met Val Glu Gly Asp Gln Leu
            35                  40                  45

Gln Lys Asp Gln Ala Phe Pro Val Leu Tyr Glu Met Leu Gln Gln Ser
        50                  55                  60

Phe Asn Leu Phe Tyr Thr Glu His Ser Ser Ala Ala Trp Asp Thr Thr
 65                  70                  75                  80
```

```
Leu Leu Glu Gln Leu Cys Thr Gly Leu Gln Gln Gln Leu Asp His Leu
                85                  90                  95

Asp Thr Cys Arg Gly Gln Gly Met Gly Glu Glu Asp Ser Glu Leu Gly
            100                 105                 110

Asn Met Asp Pro Ile Val Thr Val Lys Lys Tyr Phe Gln Gly Ile Tyr
            115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170
```

<210> SEQ ID NO 6
<211> LENGTH: 172
<212> TYPE: PRT
<213> ORGANISM: ovine

<400> SEQUENCE: 6

```
Cys Tyr Leu Ser Arg Lys Leu Met Leu Asp Ala Arg Glu Asn Leu Lys
  1               5                  10                  15

Leu Leu Ala Arg Met Asn Arg Leu Ser Pro His Ser Cys Leu Gln Asp
                 20                  25                  30

Arg Lys Asp Phe Gly Leu Pro Gln Glu Met Val Glu Gly Asp Gln Leu
             35                  40                  45

Gln Lys Asp Gln Ala Phe Pro Val Leu Tyr Glu Met Leu Gln Gln Ser
         50                  55                  60

Phe Asn Leu Phe Tyr Thr Glu His Ser Ser Ala Ala Trp Asp Thr Thr
 65                  70                  75                  80

Leu Leu Glu Gln Leu Cys Thr Gly Leu Gln Gln Gln Leu Asp His Leu
                 85                  90                  95

Asp Thr Cys Arg Gly Gln Gly Met Gly Glu Glu Asp Ser Glu Leu Gly
            100                 105                 110

Asn Met Asp Pro Ile Val Thr Val Lys Lys Tyr Phe Gln Gly Ile Tyr
            115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170
```

<210> SEQ ID NO 7
<211> LENGTH: 172
<212> TYPE: PRT
<213> ORGANISM: ovine

<400> SEQUENCE: 7

```
Cys Tyr Leu Ser Arg Lys Leu Met Leu Asp Ala Arg Glu Asn Leu Lys
  1               5                  10                  15

Leu Leu Asp Arg Met Asn Arg Ile Ser Pro His Ser Cys Leu Gln Asp
                 20                  25                  30

Arg Lys Asp Phe Gly Leu Pro Gln Glu Met Val Glu Gly Asp Gln Leu
             35                  40                  45

Gln Lys Asp Gln Ala Phe Pro Val Leu Tyr Glu Met Leu Gln Gln Ser
         50                  55                  60
```

```
Phe Asn Leu Phe Tyr Thr Glu His Ser Ser Ala Ala Trp Asp Thr Thr
 65                  70                  75                  80

Leu Leu Glu Gln Leu Cys Thr Gly Leu Gln Gln Leu Asp His Leu
                 85                  90                  95

Asp Thr Cys Arg Gly Gln Gly Met Gly Glu Glu Asp Ser Glu Leu Gly
            100                 105                 110

Asn Met Asp Pro Ile Val Thr Val Lys Lys Tyr Phe Gln Gly Ile Tyr
            115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170

<210> SEQ ID NO 8
<211> LENGTH: 172
<212> TYPE: PRT
<213> ORGANISM: ovine

<400> SEQUENCE: 8

Cys Tyr Leu Ser Arg Lys Leu Met Leu Asp Ala Arg Glu Asn Leu Lys
  1               5                  10                  15

Leu Leu Asp Arg Met Asn Arg Leu Ser Leu His Ser Cys Leu Gln Asp
                 20                  25                  30

Arg Lys Asp Phe Gly Leu Pro Gln Glu Met Val Glu Gly Asp Gln Leu
            35                  40                  45

Gln Lys Asp Gln Ala Phe Pro Val Leu Tyr Glu Met Leu Gln Gln Ser
        50                  55                  60

Phe Asn Leu Phe Tyr Thr Glu His Ser Ser Ala Ala Trp Asp Thr Thr
 65                  70                  75                  80

Leu Leu Glu Gln Leu Cys Thr Gly Leu Gln Gln Leu Asp His Leu
                 85                  90                  95

Asp Thr Cys Arg Gly Gln Gly Met Gly Glu Glu Asp Ser Glu Leu Gly
            100                 105                 110

Asn Met Asp Pro Ile Val Thr Val Lys Lys Tyr Phe Gln Gly Ile Tyr
            115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170

<210> SEQ ID NO 9
<211> LENGTH: 172
<212> TYPE: PRT
<213> ORGANISM: ovine

<400> SEQUENCE: 9

Cys Tyr Leu Ser Arg Lys Leu Met Leu Asp Ala Arg Glu Asn Leu Lys
  1               5                  10                  15

Leu Leu Asp Arg Met Asn Arg Leu Ser Pro His Ser Cys Leu Lys Asp
                 20                  25                  30

Arg Lys Asp Phe Gly Leu Pro Gln Glu Met Val Glu Gly Asp Gln Leu
            35                  40                  45
```

```
Gln Lys Asp Gln Ala Phe Pro Val Leu Tyr Glu Met Leu Gln Gln Ser
     50                  55                  60

Phe Asn Leu Phe Tyr Thr Glu His Ser Ser Ala Ala Trp Asp Thr Thr
 65                  70                  75                  80

Leu Leu Glu Gln Leu Cys Thr Gly Leu Gln Gln Gln Leu Asp His Leu
                 85                  90                  95

Asp Thr Cys Arg Gly Gln Gly Met Gly Glu Glu Asp Ser Glu Leu Gly
                100                 105                 110

Asn Met Asp Pro Ile Val Thr Val Lys Lys Tyr Phe Gln Gly Ile Tyr
            115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170

<210> SEQ ID NO 10
<211> LENGTH: 172
<212> TYPE: PRT
<213> ORGANISM: ovine

<400> SEQUENCE: 10

Cys Tyr Leu Ser Arg Lys Leu Met Leu Asp Ala Arg Glu Asn Leu Lys
  1               5                  10                  15

Leu Leu Asp Arg Met Asn Arg Leu Ser Pro His Ser Cys Leu Gln Asp
                 20                  25                  30

Arg His Asp Phe Gly Leu Pro Gln Glu Met Val Glu Gly Asp Gln Leu
             35                  40                  45

Gln Lys Asp Gln Ala Phe Pro Val Leu Tyr Glu Met Leu Gln Gln Ser
     50                  55                  60

Phe Asn Leu Phe Tyr Thr Glu His Ser Ser Ala Ala Trp Asp Thr Thr
 65                  70                  75                  80

Leu Leu Glu Gln Leu Cys Thr Gly Leu Gln Gln Gln Leu Asp His Leu
                 85                  90                  95

Asp Thr Cys Arg Gly Gln Gly Met Gly Glu Glu Asp Ser Glu Leu Gly
                100                 105                 110

Asn Met Asp Pro Ile Val Thr Val Lys Lys Tyr Phe Gln Gly Ile Tyr
            115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170

<210> SEQ ID NO 11
<211> LENGTH: 516
<212> TYPE: DNA
<213> ORGANISM: ovine

<400> SEQUENCE: 11
tgctacctgt cgcgaaaact gatgctggac gctcgacgta atttaaaact gctggaccgt      60
atgaatcgat tgtctccgca cagctgcctg caagaccgga aagcttcgg  tctgccgcag     120 gaaatggttg aaggtgacca actgcaaaaa gaccaagctt tcccggtact gtatgaaatg     180
```

```
ctgcagcagt ctttcaacct gttctacact gaacattctt cggccgcttg ggacactact      240
cttctagaac aactgtgcac tggtctgcaa cagcaactgg accatctgga cacttgccgt      300
ggccagggta tgggtgaaga agactctgaa ctgggtaaca tggatccgat cgttactgtt      360
aaaaaatatt tccagggtat ctacgactac ctgcaggaaa aaggttactc tgactgcgct      420
tgggaaatcg tacgcgttga aatgatgcgg gccctgactg tgtcgactac tctgcaaaaa      480
cggttaacta aatgggtggg tgacctgaat tctccg                                 516

<210> SEQ ID NO 12
<211> LENGTH: 516
<212> TYPE: DNA
<213> ORGANISM: ovine

<400> SEQUENCE: 12
tgctacctgt cgcgaaaact gatgctggac gctcgagaaa atttaatgct gctggaccgt       60
atgaatcgat tgtctccgca cagctgcctg caagaccgga aagacttcgg tctgccgcag      120
gaaatggttg aaggtgacca actgcaaaaa gaccaagctt cccggtact gtatgaaatg       180 ctgcagcagt ctttcaacct gttctacact gaacattctt cggccgcttg ggacactact      240
cttctagaac aactgtgcac tggtctgcaa cagcaactgg accatctgga cacttgccgt      300
ggccagggta tgggtgaaga agactctgaa ctgggtaaca tggatccgat cgttactgtt      360
aaaaaatatt tccagggtat ctacgactac ctgcaggaaa aaggttactc tgactgcgct      420
tgggaaatcg tacgcgttga aatgatgcgg gccctgactg tgtcgactac tctgcaaaaa      480
cggttaacta aatgggtggg tgacctgaat tctccg                                 516

<210> SEQ ID NO 13
<211> LENGTH: 516
<212> TYPE: DNA
<213> ORGANISM: ovine

<400> SEQUENCE: 13
tgctacctgt cgcgaaaact gatgctggac gctcgagaaa atttaaaact gctggcccgt       60
atgaatcgat tgtctccgca cagctgcctg caagaccgga aagacttcgg tctgccgcag      120
gaaatggttg aaggtgacca actgcaaaaa gaccaagctt cccggtact gtatgaaatg       180 ctgcagcagt ctttcaacct gttctacact gaacattctt cggccgcttg ggacactact      240
cttctagaac aactgtgcac tggtctgcaa cagcaactgg accatctgga cacttgccgt      300
ggccagggta tgggtgaaga agactctgaa ctgggtaaca tggatccgat cgttactgtt      360
aaaaaatatt tccagggtat ctacgactac ctgcaggaaa aaggttactc tgactgcgct      420
tgggaaatcg tacgcgttga aatgatgcgg gccctgactg tgtcgactac tctgcaaaaa      480
cggttaacta aatgggtggg tgacctgaat tctccg                                 516

<210> SEQ ID NO 14
<211> LENGTH: 516
<212> TYPE: DNA
<213> ORGANISM: ovine

<400> SEQUENCE: 14
tgctacctgt cgcgaaaact gatgctggac gctcgagaaa atttaaaact gctggaccgt       60
atgaatcgaa tttctccgca cagctgcctg caagaccgga aagacttcgg tctgccgcag      120
gaaatggttg aaggtgacca actgcaaaaa gaccaagctt cccggtact gtatgaaatg       180 ctgcagcagt ctttcaacct gttctacact gaacattctt cggccgcttg ggacactact      240
```

```
cttctagaac aactgtgcac tggtctgcaa cagcaactgg accatctgga cacttgccgt    300
ggccagggta tgggtgaaga agactctgaa ctgggtaaca tggatccgat cgttactgtt    360
aaaaaatatt tccagggtat ctacgactac ctgcaggaaa aaggttactc tgactgcgct    420
tgggaaatcg tacgcgttga aatgatgcgg gccctgactg tgtcgactac tctgcaaaaa    480
cggttaacta aaatgggtgg tgacctgaat tctccg                              516

<210> SEQ ID NO 15
<211> LENGTH: 516
<212> TYPE: DNA
<213> ORGANISM: ovine

<400> SEQUENCE: 15
tgctacctgt cgcgaaaact gatgctggac gctcgagaaa atttaaaact gctggaccgt    60
atgaatcgat tgtctctgca cagctgcctg caagaccgga aagacttcgg tctgccgcag    120
gaaatggttg aaggtgacca actgcaaaaa gaccaagctt tcccggtact gtatgaaatg    180
ctgcagcagt ctttcaacct gttctacact gaacattctt cggccgcttg ggacactact    240
cttctagaac aactgtgcac tggtctgcaa cagcaactgg accatctgga cacttgccgt    300
ggccagggta tgggtgaaga agactctgaa ctgggtaaca tggatccgat cgttactgtt    360
aaaaaatatt tccagggtat ctacgactac ctgcaggaaa aaggttactc tgactgcgct    420
tgggaaatcg tacgcgttga aatgatgcgg gccctgactg tgtcgactac tctgcaaaaa    480
cggttaacta aaatgggtgg tgacctgaat tctccg                              516

<210> SEQ ID NO 16
<211> LENGTH: 516
<212> TYPE: DNA
<213> ORGANISM: ovine

<400> SEQUENCE: 16
tgctacctgt cgcgaaaact gatgctggac gctcgagaaa atttaaaact gctggaccgt    60
atgaatcgat tgtctccgca cagctgcctg aaggaccgga aagacttcgg tctgccgcag    120
gaaatggttg aaggtgacca actgcaaaaa gaccaagctt tcccggtact gtatgaaatg    180
ctgcagcagt ctttcaacct gttctacact gaacattctt cggccgcttg ggacactact    240
cttctagaac aactgtgcac tggtctgcaa cagcaactgg accatctgga cacttgccgt    300
ggccagggta tgggtgaaga agactctgaa ctgggtaaca tggatccgat cgttactgtt    360
aaaaaatatt tccagggtat ctacgactac ctgcaggaaa aaggttactc tgactgcgct    420
tgggaaatcg tacgcgttga aatgatgcgg gccctgactg tgtcgactac tctgcaaaaa    480
cggttaacta aaatgggtgg tgacctgaat tctccg                              516

<210> SEQ ID NO 17
<211> LENGTH: 516
<212> TYPE: DNA
<213> ORGANISM: ovine

<400> SEQUENCE: 17
tgctacctgt cgcgaaaact gatgctggac gctcgagaaa atttaaaact gctggaccgt    60
atgaatcgat tgtctccgca cagctgcctg caagaccggc acgacttcgg tctgccgcag    120
gaaatggttg aaggtgacca actgcaaaaa gaccaagctt tcccggtact gtatgaaatg    180
ctgcagcagt ctttcaacct gttctacact gaacattctt cggccgcttg ggacactact    240
```

-continued

```
cttctagaac aactgtgcac tggtctgcaa cagcaactgg accatctgga cacttgccgt    300
ggccagggta tgggtgaaga agactctgaa ctgggtaaca tggatccgat cgttactgtt    360
aaaaaatatt tccagggtat ctacgactac ctgcaggaaa aaggttactc tgactgcgct    420
tgggaaatcg tacgcgttga aatgatgcgg gccctgactg tgtcgactac tctgcaaaaa    480
cggttaacta aaatgggtgg tgacctgaat tctccg                              516
```

```
<210> SEQ ID NO 18
<211> LENGTH: 172
<212> TYPE: PRT
<213> ORGANISM: ovine

<400> SEQUENCE: 18

Cys Tyr Leu Ser Gln Lys Leu Met Leu Asp Ala Arg Glu Asn Leu Lys
  1               5                  10                  15

Leu Leu Asp Arg Met Asn Arg Leu Ser Pro His Ser Cys Leu Gln Asp
             20                  25                  30

Arg Lys Asp Phe Gly Leu Pro Gln Glu Met Val Glu Gly Asp Gln Leu
         35                  40                  45

Gln Lys Asp Gln Ala Phe Pro Val Leu Tyr Glu Met Leu Gln Gln Ser
     50                  55                  60

Phe Asn Leu Phe Tyr Thr Glu His Ser Ser Ala Ala Trp Asp Thr Thr
 65                  70                  75                  80

Leu Leu Glu Gln Leu Cys Thr Gly Leu Gln Gln Gln Leu Asp His Leu
                 85                  90                  95

Asp Thr Cys Arg Gly Gln Gly Met Gly Glu Glu Asp Ser Glu Leu Gly
            100                 105                 110

Asn Met Asp Pro Ile Val Thr Val Lys Lys Tyr Phe Gln Gly Ile Tyr
        115                 120                 125

Asp Tyr Leu Gln Glu Lys Gly Tyr Ser Asp Cys Ala Trp Glu Ile Val
    130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170
```

```
<210> SEQ ID NO 19
<211> LENGTH: 172
<212> TYPE: PRT
<213> ORGANISM: ovine

<400> SEQUENCE: 19

Cys Tyr Leu Ser Arg Thr Leu Met Leu Asp Ala Arg Glu Asn Leu Lys
  1               5                  10                  15

Leu Leu Asp Arg Met Asn Arg Leu Ser Pro His Ser Cys Leu Gln Asp
             20                  25                  30

Arg Lys Asp Phe Gly Leu Pro Gln Glu Met Val Glu Gly Asp Gln Leu
         35                  40                  45

Gln Lys Asp Gln Ala Phe Pro Val Leu Tyr Glu Met Leu Gln Gln Ser
     50                  55                  60

Phe Asn Leu Phe Tyr Thr Glu His Ser Ser Ala Ala Trp Asp Thr Thr
 65                  70                  75                  80

Leu Leu Glu Gln Leu Cys Thr Gly Leu Gln Gln Gln Leu Asp His Leu
                 85                  90                  95

Asp Thr Cys Arg Gly Gln Gly Met Gly Glu Glu Asp Ser Glu Leu Gly
            100                 105                 110
```

```
Asn Met Asp Pro Ile Val Thr Val Lys Lys Tyr Phe Gln Gly Ile Tyr
        115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170

<210> SEQ ID NO 20
<211> LENGTH: 172
<212> TYPE: PRT
<213> ORGANISM: ovine

<400> SEQUENCE: 20

Cys Tyr Leu Ser Arg Lys Leu Met Leu Asp Ala Arg Glu Asn Leu Lys
  1               5                  10                  15

Leu Leu Asp Gln Met Asn Arg Leu Ser Pro His Ser Cys Leu Gln Asp
                 20                  25                  30

Arg Lys Asp Phe Gly Leu Pro Gln Glu Met Val Glu Gly Asp Gln Leu
             35                  40                  45

Gln Lys Asp Gln Ala Phe Pro Val Leu Tyr Glu Met Leu Gln Gln Ser
         50                  55                  60

Phe Asn Leu Phe Tyr Thr Glu His Ser Ser Ala Ala Trp Asp Thr Thr
 65                  70                  75                  80

Leu Leu Glu Gln Leu Cys Thr Gly Leu Gln Gln Gln Leu Asp His Leu
                 85                  90                  95

Asp Thr Cys Arg Gly Gln Gly Met Gly Glu Glu Asp Ser Glu Leu Gly
                100                 105                 110

Asn Met Asp Pro Ile Val Thr Val Lys Lys Tyr Phe Gln Gly Ile Tyr
        115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170
```

US 6,833,256 B1

INTERFERON TAU MUTANTS AND METHODS FOR MAKING THEM

This application claims benefit of U.S. Provisional Appl. No. 60/140,411 filed Jun. 22, 1999.

FIELD OF THE INVENTION

The present invention is directed to the field of animal and human health, and more particularly to pharmacological uses of analogs or mutants of interferon-tau (IFN-τ) that differ from native IFN-τ because of substitutions of amino acids near the amino terminus of the IFN-τ molecule that impart improved biological activity. The IFN-τ mutants described in this disclosure have low toxicity, retain the same or slightly reduced antiviral activity compared with highly effective IFN-alpha, and have enhanced antiproliferative activity compared to native IFN-tau, making them useful in treating viral infections, cancer, and immune system diseases including autoimmune diseases. The present invention is also directed to a method for making novel recombinant proteins, especially interferons, interleukins, and cytokines, polypeptide hormones and other biopharmaceuticals that have improved biological activity over known proteins and/or lower toxicity and/or increased stability.

REFERENCES

1. Pestka, S., Langer, J. A., Zoon, K. C., and Samuel, C. E. (1987) *Ann. Rev. Biochem.* 56, 727–777
2. Spencer, T. E., Becker, W. C. George, P., Mirando, M. A., Ogle, T. F., and Bazer, F. W. (1995) *Endocrin.* 136, 4932–4944
3. Bazer, F. W., Spencer, T. E., and Ott, T. L. (1996) *American J. Reprod. Immunol.* 35, 297–308
4. Imakawa, K., Anthony, R. V., Kazemi, M., Marotti, K. R., Polites, H. G., and Roberts, R. M. (1987) *Nature* 330, 377–379
5. Roberts, R. M., Cross, J. S. and Leaman, D. W. (1992) *Endocr. Rev.* 13, 432–452
6. Alexenko, A. P., Leaman, D. W., Li, J., and Roberts, R. M. (1997) *J. Interferon Cytokine Res.* 17, 769–799
7. Alexenko, A. P., Ealy, A. D., and Roberts, R. M. (1999) *J. Interferon Cytokine Res.* 19, 1335–1341
8. Subramaniam, P. S., Khan, S. A., Pontzer, C. H., and Johnson, H. M. (1995) *Proc. Natl. Acad. Sci. U.S.A.* 92, 12270–12274
9. Pontzer, C. H., Yamamoto, J. K., Bazer, F. W., Ott, T. L., and Johnson, H. M. (1997) *J. Immunol.* 158, 4351–4357
10. Soos, J. M., Subramaniam, P. S., Hobeika, A. C., Schiffenbauer, J. and Johnson, H. M. (1995) *J. Immunol.* 155, 2747–2753
11. Radhakrishnan, R., Walter, L. J., Hruza, A., Reichert, P., Trotta, P. P., Nagabhushan, T. L., and Walter, M. R. (1996) *Structure* 4, 1453–1463
12. Senda, T., Saitoh, S.-I., and Mitsui, Y. (1995) *J. Mol. Biol.* 253, 187–207
13. Karpusas, M., Nolte, M., Benton, C. B., Meier, W., Lipscomp, W. N. and Goetz, S. (1997) *Proc. Natl. Acad. Sci. U.S.A.* 94, 11813–11818
14. Radhakrishnan, R., Walter, L. J., Subramaniam, P. S., Johnson, H. M., and Walter, M. R. (1999) *J. Mol. Biol.* 286, 151–162
15. Mitsui, Y., Senda, T., Shimazu, T., Matsuda, S., and Utsumi, J. (1993) *Pharmacol. Ther.* 58, 93–132
16. Runkel, L., Pfeffer, L., Lewerenz, M., Monneron, D., Yang, C. H., Murti, A., Pellegrini, S., Geolz, S., Uzé, G., and Morgensen, K. (1998) *J. Biol. Chem.* 273, 8003–8008
17. Pontzer, C. H., Ott, T. L., Bazer, F. W., and Johnson, H. M. (1990) *Proc. Natl. Acad. Sci. U.S.A.* 87, 5945–5949
18. Li, J., and Roberts, R. M. (1994) *J. Biol. Chem.* 269, 24826–24833
19. Van Heeke, G., Ott, T. L., Strauss, A., Ammaturo, D., and Bazer, F. W. (1996) *J. Interferon Cytokine Res.* 16, 119–126
20. Swann, S. L., Bazer, F. W., Villarete, L. H., Chung, A., and Pontzer, C. H. (1999) *Hybridoma* 18, 399–405
21. Li, J., and Roberts, R. M. (1994) *J. Biol. Chem.* 269, 13544–13550
22. Pontzer, C. H., and Johnson, H. M. (1995) *Meth. Neurosci.* 24, 3–9
23. Zoon, K. C., Miller, D. M., Bekisz, J., zur Nedden, D., Enterline, J. C. Nguyen, N. Y., and Hu, R-Q. (1992) *J. Biol. Chem.* 267, 15210–15219
24. Johnson, J. A., Hochkeppel, H-K., and Gangemi, J. D. (1999) *J. Interferon Cytokine Res.* 19, 1107–1116
25. Aguet, M., Grobke, M., and Dreiding, P. (1984) *Virol.* 132, 211–216
26. Mogensen, K. E., Lewerenz, M., Reboul, J., Lutfalla, G., and Uzé, G. (1999) *J. Interferon Cytokine Res.* 19, 1069–1098
27. Syed, R. S., Reid, S. W., Li, C., Cheetham, J. C., Aoki, K. H., et al. (1998) *Nature* 395, 511–516
28. Domanski, P., Nadeau, W. W., Platanias, L. C., Fish, E., Kellum, M., Pitha, P., and Colamonici, O. R. (1998) *J. Biol. Chem.* 273, 3144–3147
29. Harada, H., Taniguchi, T., and Tanaka, N. (1998) *Biochimie* 80, 641–650
30. Stancato, L. F., Yu, C-R., Petricoin, III, E. F., and Larner, A. C. (1998) *J. Biol. Chem.* 273, 18701–18704
31. Petricoin, III, E. F., Ito, S., Williams, B., Audet, S., Stancato, L. F. et al. (1997) *Nature* 390, 629–632
32. Uddin, S., Fish, E. N., Sher, D. A., Gardziola, C., White, M. F., and Platanias, L. C. (1997) *J. Immunol.* 158, 2390–2397
33. Barasoain, I., Portolés, A., Aramburu, J. F., and Rojo, J. M. (1989) *J. Immunol.* 143, 507–512
34. Arora, T., Floyd-Smith, G., Espy, M. J., and Jelinek, D. F. (1999) *J. Immunol.* 162, 3289–3297
35. Waine, G. J., Tymms, M. J., Brandt, E. R., Cheetham, B. F., and Linnane, A. W. (1992) *J. Interferon Cytokine Res.* 12, 43–48.

INTRODUCTION

The term "interferon" generically refers to a group of vertebrate glycoproteins and proteins that are known to have various biological activities, including antiviral, antiproliferative, and immunomodulatory properties at least in the species of animal from which such substances are derived and sometimes the interferons have cross species activity. The following definition of interferon has been accepted by an international committee assembled to devise a system for the orderly nomenclature of interferons: "To qualify as an interferon a factor must be a protein which exerts virus nonspecific, antiviral activity at least in homologous cells through cellular metabolic processes involving synthesis of both RNA and protein." Journal of Interferon Research, 1, pp. vi (1980). "Interferon" as used to describe the present invention shall be deemed to have that definition. The type I interferons (IFN-α, -β, -ω, and -τ) are a group of proteins produced by the body to defend cells by inhibiting viral replication and decreasing cell proliferation.

IFN-alphas have been shown to inhibit various types of cellular proliferation. IFN.alpha.'s are especially useful against hematologic malignancies such as hairy-cell leukemia (Quesada, et al., 1984). Further, these proteins have also shown activity against multiple myeloma, chronic lymphocytic leukemia, low-grade lymphoma, Kaposi's sarcoma, chronic myelogenous leukemia, renal-cell carcinoma, urinary bladder tumors and ovarian cancers (Bonnem, et al., *J. Bio. Response Modifiers* 3:580(1984); Oldham, *Hospital Practice* 20:71(1985). The role of interferons and interferon receptors in the pathogenesis of certain autoimmune and inflammatory diseases has also been investigated (Benoit, et al., *J. Immunol* 150(3):707(1993).

IFN-alphas are also useful against various types of viral infections (Finter, et al., *Drugs* 42(5):749(1991). Alpha interferons have shown activity against human papillomavirus infection, Hepatitis B, and Hepatitis C infections (Finter, et al., 1991; Kashima, et al., (*Laryngoscope* 98:334 (1988); Dusheiko, et al. *J. Hematology* 3 (suppl.2):S199 (1986); Davis, et al., *N. England J. Med.* 321:1501(1989). The journal articles listed in this application are all incorporated in their entirety.

Interferons of the alpha type (IFN-αs) are FDA-approved for the treatment of several diseases, including chronic hepatitis B and C, genital warts, hairy cell leukemia, and Kaposi's sarcoma. They are in clinical trials for AIDS and cancers, including non-Hodgkin's lymphoma and malignant melanoma (Mariano, T. M., *Interferons: Principles and Medical Applications*, 1992, 129–138(1992), chronic myelogenous leukemia, cutaneous squamous cell carcinoma, and laryngeal papillomatosis (Baron, S., *JAMA* 10, 1375–83 (1991).

IFNs are also able to aid the body by acting in an immunomodulatory role. For example, type I IFNs have been shown to increase macrophage phagocytic activity and nitrous oxide mediated killing as well as regulate IFN-γ production (Reder, A., *Interferon Therapy of Multiple Sclerosis*, 61–64, 485–492(1997). Like other type I interferons, IFN-τ production has also been shown to increase natural killer cell activity (Tuo, W., *American Journal of Reproductive Immunology*, 29, 26–34(1993).

However, IFN-α therapy has its drawbacks, as patients often suffer side effects of the treatment, which may be severe. Side effects are dose-dependent, and low dose side effects include flu-like symptoms which frequently interfere with normal activity, while higher doses may induce nausea, vomiting, anorexia, and rashes (Pontzer, et al., *Cancer Res.* 51:5304(1991). Extremely high doses appear to cause peripheral neuropathy and thrombocytopenia. It has also been previously demonstrated that in vivo treatment with IFN-β and IFNα in humans and animals causes toxicity manifested as a number of side effects including fever, lethargy, tachycardia, weight loss, and leukopenia. These side effects often require (i) the interferon dose to be reduced to levels that limit the effectiveness of treatment, or (ii) termination of the treatment. Thus, treatment with alpha interferons is constrained both by patient compliance and the inability to use high doses in a sustained fashion. Adverse effects of IFN-beta are similar to those seen with IFN-alpha. IFN-beta has been used for treatment of multiple sclerosis.

A more recently discovered type 1 interferon, interferon-tau (IFN-τ), has lower toxicity than IFN-α while also displaying antiviral and antiproliferative activities. Ovine IFN-τ is a major conceptus secretory protein produced by the embryonic trophectoderm during the critical period of maternal recognition in sheep. It is produced and secreted in large amounts for a short time prior to implantation. Its principle role in sheep and other ruminants is to prevent regression of the corpus luteum by inhibiting estrogen receptor upregulation and blocking the pulsatile secretion of prostaglandin F2 alpha.

Relative to other interferons, ovine IFN-tau. shares about 45 to 68% amino acid homology with Interferon-alpha and the greatest sequence similarity with the interferon-omega-s (IFN omega-s) of about 68%. Ovine IFN-τ has about 50% sequence homology to interferon α, with the closest homology in the carboxy terminal region of the molecule. Like IFN-alpha, FN-T also has five helices. The amino acid sequence for human IFN αA is provided as SEQ. ID NO. 1. The amino acid sequence for native ovine IFNτ 1mod is provided as SEQ. ID NO. 2 and its nucleic acid sequence is SEQ. ID NO. 3.

There has been significant interest in finding functionally important sites on Type I IFNs, and in developing novel IFNs with improved biological activity, significant cross species activity and low toxicity for clinical use in treating immune diseases and cancer.

SUMARY OF THE INVENTION

It is an object of the present invention to provide a method for making a recombinant protein having improved biological activity by changing one or more amino acids in a first protein with a known biological activity, which amino acids differ from corresponding amino acids in a structurally similar second protein having the desired biological activity, to the differing one or more amino acids found in the second protein, in order to produce a compound with an improved biological activity. In a preferred embodiment the differing amino acids are in an area of the molecule with a known biological activity. The recombinant proteins can be any protein, especially interferons, interleukins, cytokines, polypeptide hormones or other biopharmaceuticals. In one embodiment, the first and second proteins are type one interferons, including interferon tau, alpha and beta and omega. In another embodiment, the first protein is interferon-tau and the second protein is interferon-alpha.

It is a further object of this invention to provide recombinant proteins with enhanced antiviral and/or antiproliferative activity, or lower cytotoxicity.

In a further object of the invention, the amino acid substitutions are chosen by identifying solvent-exposed amino acids in the first and second proteins, and making amino acid substitutions in the first protein by inserting the differing solvent-exposed amino acids that were identified in the second protein. The first and second proteins in the method of the present invention may be from the same or different species, and may be naturally occurring or non-naturally occurring.

Another objective of the present invention is to provide novel interferon-tau mutant proteins with low cytotoxicity for use in treating or preventing cancer, immune system diseases including autoimmune diseases such as Type I diabetes mellitus, rheumatoid arthritis, lupus erythematosus and psoriasis; and viral infections, or for any other use that interferons may generally be put to. The novel interferon-tau mutants of the present invention are identified by amino acid SEQ. ID NOs. 4–10, and 18–20.

It is another object to provide (a) a method for treating cancer or a tumor, comprising administering to an animal in need of such treatment, a therapeutically effective amount of a recombinant interferon tau protein selected from the group comprising amino acid sequences identified by SEQ. ID NOs. 4–10, and 18–20, sufficient to treat the cancer; including human adenocarcinoma, treat breast cancer, prostate cancer, glioblastomas, melanomas, myelomas, lymphomas, leukemias, lung cancer, skin cancer, bladder cancer, kidney cancer, brain cancer, ovarian cancer, pancreatic cancer, uterine cancer, bone cancer, colorectal cancer, cervical cancer and neuroectodermal cancer, and premalignant conditions, including, without limitation, monoclonal gammapothies, dysplasia, including, without limitation, cervical and oral dysplasia. (b) a method of treating a viral disease, comprising administering to an animal in need of such treatment, a therapeutically effective amount of a recombinant interferon tau protein selected from the group comprising amino acid sequences identified by SEQ. ID NOs. 4–10, and 18–20, sufficient to treat the viral disease as enumerated in the detailed description of this invention and including RNA and DNA viruses, HIV, and Hepatitis B and C, especially; (d) a method of decreasing tumor cell growth, comprising contacting tumor cells in vivo or in vitro, with a recombinant IFN-tau protein selected from the group comprising amino acid sequences identified by SEQ. ID NOs. 4–10, and 18–20, at a concentration effective to decrease growth of the tumor cells.

DETAILED DESCRIPTION OF THE INVENTION

Definitions

Interferon: An interferon is a protein which exerts virus nonspecific, antiviral activity at least in homologous cells through cellular metabolic processes involving synthesis of both RNA and protein.

Structural Similarity: For the purpose of the present disclosure, a first protein is considered structurally similar to a second protein if the first and second proteins (1) bind to the same receptor, even though the affinity for the receptor may be different, or (2) if the first and second protein have the same or similar biological activity, or (3) if their X-ray crystallographic structures can be superimposed with a root mean square difference of 3 angstroms or less over any portion of the molecule, or (4) if the two proteins have at least 25% identity as defined herein.

Interferon-.tau. (IFN-tau.) refers to any one of a family of interferon proteins having greater than 70% amino acid sequence homology to the ovine IFN-tau1mod having. Amino acid homology can be determined using, for example, the LALIGN program with default parameters. This program is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.). Typically, IFN-tau. has at least one characteristic from the following group of characteristics: (a) expressed during embryonic/fetal stages by trophectoderm/placenta, (b) anti-luteolytic properties, (c) anti-viral properties, and (d) anti-cellular proliferation properties. IFN-tau. can be obtained from a number of sources including cows, sheep, ox, and reportedly also in humans.

Ovine interferon-.tau. (Ovine IFN-tau.) is a major conceptus secretory protein produced by the embryonic trophectoderm during the critical period of maternal recognition in sheep. One form of interferon-tau is Ovine IFN-tau1mod which is 172 amino acids in length (SEQ ID NO:2), and has a nucleic acid sequence as set forth in SEQ. ID. NO. 1. Because of redundancy in the genetic code, the base sequence for interferon tau 1 mod can be any base sequence that encodes the 172 amino acids of SEQ. ID NO.2.

Mutant (i.e., recombinant) interferon tau proteins of the present invention include but are not limited to proteins having one of the amino acid sequences set forth in SEQ ID NOS. 2, and 4–10.

Mutant interferon tau DNA of the present invention is any nucleic acid sequence producing the mutant interferon tau proteins of the present invention, including but not limited to SEQ. ID NOS. 11–17.

Percent (%) identity, with respect to two amino acid sequences [or nucleic acid sequences], refers to the % of residues that are identical in the two sequences when the sequences are optimally aligned and no penalty is assigned to "gaps". In other words, if a gap needs to be inserted into a first sequence to optimally align it with a second sequence, the % identity is calculated using only the residues that are paired with a corresponding amino acid residue (i.e., the calculation does not consider residues in the second sequences that are in the "gap" of the first sequence). Optimal alignment is defined as the alignment giving the highest % identity score. Such alignments can be preformed using the "GENEWORKS" program. Alternatively, alignments may be performed using the local alignment program LALIGN with a ktup of 1, default parameters and the default PAM.

Treating a disease refers to administering a therapeutic substance effective to reduce the symptoms of the disease and/or lessen the severity of the disease or has other effects beneficial to the patient.

DETAILED DESCRIPTION

In one preferred embodiment of the present invention, the inventive strategy involves changing amino acids near the amino terminus of mature ovine interferon-tau 1mod (IFN-τ) that are exposed to solvent and differ from the corresponding amino acid found in the same position in an human IFN-αA (or other interferon alpha analog), to the amino acid found in human IFN-αA, in order to produce a compound with a better ratio of therapeutic activity to toxicity than is found in either human IFN-αA or ovine IFN-τ 1mod.

In the specific embodiments described here, ovine IFN-τ isoform 1 mod (GenBank accession number P08316) was used, as was human IFN-α type 2, also known as type A or leukocyte interferon (GenBank accession number IVHUA2). However, changing the solvent-exposed amino acids of any class or isoform of IFN-τ to the corresponding amino acids found in any class or isoform of IFN-α is covered by this invention. Furthermore, the invention covers changing multiple amino acids in an IFN-τ to those found in an IFN-α and all possible combinations of changes and changes in cytokines, polypeptide hormones, and biopharmaceuticals of any type.

Cytokines include: Monocyte Chemoattractant Protein-1, Interleukin-1α, Interleukin -1β, (IL-1α, IL-1β, and IL-1ra), Interleukin-8 (IL-8), Interleukin-9 (IL-9), Interleukin-2 (IL-2), Inter-leukin-10 (IL-10), Interleukin-3 (IL-3), Interleukin-11 (IL-11), Interleukin-12 (IL-12), Interleukin-4 (IL-4), Interleukin-13 (IL-13), High Molecular Weight B Cell Growth Factor (Interleukin-14), Interleukin-5 (IL-5), Human B Cell Growth Factor-12 kDa (BCGF-12 kDa), Interleukin-6 (IL-6), CD40 Ligand (CD40L), Tumour Necrosis Factor (TNF), Interleukin-7 (IL-7), Tumour Necrosis Factor-β, The Macrophage Colony-Stimulating Factor (M-CSF), Interferon-Gamma (IFNγ), Granulocyte-Macrophage Colony-Stimulating Factor (GM-CSF), Leukemia Inhibitory Factor (LIF), Onocostatin M (OSM), Stem Cell Factor (SCF), Hepatocyte Growth Factor, Ciliary Neurotrophic Factor (CNTF), Neurotrophins, The Epidermal Growth Factor (EGF), Neu Differentiration Factor (NDF), Neuregulin (NRG) Family, Neu/ErbB-2 Receptor, Platelet-derived Growth Factor (PDGF), Erythropoietin, Granulocyte Colony-Stimulating Factor, Insulin-like Growth Factors (IGFs), Granulocyte Colony-Stimulating Factor, Fibroblast Growth Factors (FGFs), Colony-Stimulating Factor-1 (CSF-1), Vascular Endothelial Growth Factor, Transforming Growth Factor-β (TGFβ), Endothelin.

Embodiments of this invention include novel mutants of IFNτ that have increased anti-proliferative effects and/or antiviral effects, without increased cellular toxicity compared to native IFN-τ. These novel interferon mutants may thus have an improved therapeutic index compared to currently available interferon treatment. While the specific examples in the present invention are directed to mutants of ovine IFN-tau1mod, the same substitutions of amino acids from human IFN-αA or other IFN-alpha, into human IFN tau can be made and are contemplated. Mutations in the human analog of IFN-tau will have the advantage of being potentially less antigenic than mutant ovine IFN-tau.

The present invention is not limited to IFN-τ. The present methods can be used to improve biological activity of any interferon, interleukin, cytokine, chemokine, hormone, protein or peptide, for which the amino acid sequence is known and for which there is another structurally similar molecule having the desired biological activity, including naturally occurring or recombinant proteins. The structurally similar molecule can be a related protein or peptide that binds to the same receptor or chemical as the first protein that is to be modified, or that has the same or similar biological activity.

The present invention includes a method for making a recombinant protein having improved biological activity comprising: selecting a first protein for which the biological activity is to be improved, and for which the amino acid sequence is known, identifying a second protein that is structurally similar to the first protein, which second protein has the desired biological activity, and for which the amino acid sequence is known; identifying one or more amino acids on the first protein that are different from the corresponding amino acids on the second protein; substituting one or more of the differing amino acids identified in the second protein for the corresponding one or more amino acids in the first protein, to obtain the recombinant protein having improved biological activity.

In another embodiment, the present invention includes a method for designing mutants that have improved biological activity by selecting a first protein for which the biological activity is to be improved, and for which the amino acid sequence is known (such as ovine IFN-tau), and identifying a second protein that is structurally similar to the first protein, which second protein has the desired biological activity, and for which the amino acid sequences are known (such as IFN-alpha). It is then necessary to identify those amino acids on the first protein that are different from the corresponding amino acids on the second protein. In a preferred embodiment, these amino acids are in a region of the first and second proteins that is known or suggested to be associated with the desired biological activity (such as the amino terminal region of interferon alpha). Once the differing amino acids have been identified, one or more of the differing amino acids identified in the second protein (such as interferon alpha) are substituted for the corresponding one or more amino acids in the first protein (interferon tau). The amino acid substitutions are made, for example, by making one or more substitutions to the nucleic acid sequence of the first protein thereby making a mutated recombinant nucleic acid sequence including codons for the one or more substituted amino acids. Because of the redundancy of the genetic code, multiple nucleic acid sequences for a given amino acid sequence can be easily identified without undue experimentation. The present invention can employ any nucleic acid sequence that encodes a desired protein. This recombinant nucleic acid thus encodes the recombinant protein having improved biological activity. The recombinant nucleic acid can then be translated in vivo or in vitro using methods known to those skilled in the art, to obtain the recombinant protein having improved biological activity. The invention covers changing only one amino acid or multiple amino acids in the first protein to those found in the second protein, and all possible combinations of changes. Similarly the present invention includes a method for reducing undesirable biological properties by the obverse procedure. For example, replacing a toxic portion of interferon alpha with one or more specific amino acids from interferon-tau.

In a preferred embodiment, the site directed mutations are made in a known biologically active region of the first protein to be modified, based on differences between the protein to be modified and the biologically active region of the structurally similar protein.

In another embodiment of the present method, the first and second structurally similar proteins are both mutant proteins that have improved biological activity or lower toxicity or improved stability over their respective unmutated analog, and that have different amino acids from each other. These mutants need not have been made according to the present invention described above, but could be, for example, fusion proteins that have improved biological activity over the corresponding native protein. To further improve the desired biological activity of the first mutant protein, biologically targeted nucleic acid substitutions are made to the first mutant protein so that the new codon(s) encode one or more corresponding amino acids in the second mutant protein that are different, to thereby improve the biological activity of the first protein.

In another embodiment, either the first or the second protein or both are fusion proteins. In another embodiment, the fusion proteins are human/animal chimeric proteins.

Site directed mutagenesis is one method for making the mutations to the native ovine IFN-tau1mod DNA to make the desired specific amino acid substitutions in the first protein. Other methods known to those skilled in the art can be used to make the required nucleic acid changes to produce codons that express the desired amino acids. In addition, the invention also includes synthesizing the desired recombinant protein either by amino acid synthesis, or nucleic acid synthesis followed by in vivo or in vitro translation to obtain the resultant final recombinant protein. These and other objectives will be apparent from the following description of the invention.

The resultant final recombinant protein is therefore not a fusion protein. Fusion proteins that combine a desired region of a first protein and a desired region of one or more other proteins have been disclosed in the prior art. One disadvantage of fusion proteins is that one or more of the fused regions may impart an undesirable effect like increased antigenicity or cytotoxicity to the construct, in addition to the desired biological effect being sought. By changing large areas of a molecule at one time, as done in fusion proteins, it is much more likely that the structural integrity of the molecule will be disrupted or lost and that the biological activity will be similarly decreased.

One advantage of the present method for making recombinant proteins having improved biological activity is that it provides a much more refined method for making recombinant proteins having improved biological activity, compared to fusion proteins, buy making very specific biologically directed amino acid changes to the first protein.

The ovine IFN-τ 1mod mutants (also referred to as IFN-tau mutants or IFN-tau recombinant proteins or tau mutants) described in this disclosure retain the low toxicity of native IFN-tau, and have enhanced antiproliferative activity against human cell lines. Therefore in a preferred embodiment, the interferon tau mutants are useful for treating cancer and tumors as is further enumerated in the Utility section of this application. The IFN-tau mutants are also useful in treating any disease that respond to any type I interferon, including interferon alpha, beta, omega and tau, because the mutants of the present invention retain their binding capacity to the type I receptor and have similar activity to the other interferons. These uses are more fully enumerated in the Utility section below, and include immune system diseases generally, and autoimmune diseases particularly. Because of the low toxicity of the interferon tau mutants compared to other interferons, the mutants are the drug of choice. Low toxicity of the interferon tau mutants also means that the mutants can be administered at higher doses than other non-tau interferons, which is an additional advantage of the tau mutants.

The interferon tau mutants were tested in the classic assay for antiviral activity in to Madin Darby Bovine Kidney (MDBK) cells in vitro. All of the mutants displayed some antiviral activity in this assay. They are also effective in treating human viral infections, as all of them retain the low toxicity of native ovine IFN-τ 1mod and they have the same or only slightly reduced anti-viral activity on the bovine cell line.

IFN-τ, a relatively recent addition to the type I IFN family, appears to be without significant side effects in humans in phase I clinical trials for treatment of multiple sclerosis (J. M. Soos, Harvard Univ., personal communication). IFN-τ is therefore a less toxic alternative to IFN-α therapy. Toxicity associated with IFN-α was not seen with IFN-τ on a variety of different cell lines including human WISH cells, mouse L929 cells, human peripheral lymphocytes and HIV-infected human peripheral lymphocytes. Furthermore, in vivo studies in mice have shown that IFN-α associated toxicities, including lymphocyte depression and decrease in weight, were not seen with treatment by IFN-τ (Reder, 1997).

As observed for IFN-alphas, different IFN-tau subtypes exhibit different relative antiviral and antiproliferative activities (6). Several subtypes of ovine IFN-tau have also been shown to have some degree of species cross-reactivity, such as is seen with human IFN-alpha B/D (7). Further, the ovine IFN-tau1mod subtype has been used at high concentrations in vitro without producing a decrease in Madin Darby bovine kidney (MDBK) or peripheral blood cell viability (8,9). In vivo, ovine IFN-tau1mod has effectively reduced the incidence and severity of murine experimental allergic encephylomyelitis (EAE) without decreasing animal weight, white blood cell counts or lymphocyte function, complications that are observed with identical antiviral doses of murine IFN-alpha (10). Ovine IFN-tau1mod also appears to be without significant side effects in humans in Phase I clinical trials for treatment of multiple sclerosis (J. M. Soos, Harvard Univ.—personal communication). Thus ovine IFN-tau1mod retains its antiviral activity in humans across potential species barriers without causing cytotoxicity. Ovine IFN-tau1mod has also been shown to suppress papillomavirus E7 oncoprotein expression and increase p53 more effectively than did human IFÑ-alpha A or the hybrid IFN-alpha B/D (24). All of the tau mutants of the present invention can be used to treat the diseases listed above as they retain antiviral activity, antiproliferative activity, low toxicity, and the ability to bind to type I receptor.

Because of its low cytotoxicity, much interest has been generated in the medical community concerning the use of IFN-τ in treating human conditions. The use of ovine and bovine IFN-τ as antitumor agents is disclosed in U.S. Pat. No. 5,958,402. The use of ovine and bovine IFN-τ as antiviral agents is disclosed in U.S. Pat. No. 5,942,223. Recombinant production of human IFN-τ and methods of using it to treat viral conditions and tumors are disclosed in U.S. Pat. Nos. 5,705,363 and 5,738,845. Methods for using human IFN-τ to treat autoimmune diseases, including multiple sclerosis are disclosed in U.S. Pat. Nos. 5,906,816 and 6,060,450. The use of interferons for treating fibromyalgia in humans is disclosed in U.S. Pat. No. 6,036,949. Additionally, a hybrid IFN-τ/IFN-α molecule comprising the amino terminal region of human IFN-τ joined to a carboxyl terminal sequence of a non- IFN-τ type I interferon is disclosed in U.S. Pat. No. 5,939,286. All of these patents are incorporated herein in their entirety. All of the tau mutants of the present invention can be used to treat the diseases listed above as they retain antiviral activity, antiproliferative activity, low toxicity, and the ability to bind to type I receptor.

A. Structure

The activity of the type I interferons generally is determined by structure. Although all the type I IFNs share the same general structure, great sequence variation is seen even within the IFN-αs in humans (Lee, 1995). These sequence differences are probably responsible for minor structural differences and thus the variation in activity seen between the different IFNs. The primary amino acid sequence of ovine IFN-τ shares 45–55% homology with a range of human, bovine, mouse, rat, and pig IFN-αs, 30% homology with human IFN-β and 70% homology with bovine IFN-ω (Roberts, 1991). There are at least 20 different forms of IFN-α (Johnson, 1994) and at least five different isoforms of IFN-τ (Imakawa, 1987). There are nineteen amino acid residues conserved across all IFNs-α, -β and -ω and these amino acids are identical in IFN-τ (Roberts, 1992).

The structure of IFN-τ was predicted to assume a conformation similar to the other type I IFNs, exhibiting a five-helix bundle). Human IFN-alpha (26), murine IFN-β (Senda, T., *EMBO Journal* 11, 3193–3201(1992) and ovine IFN-τ (14) have now been crystallized and their structures determined. The structure of ovine IFN-τ consists of five α-helices designated Helix A (residues 4–24), B (53–74), C (80–100), D (116–133) and E (135–172) separated by loop regions AB, BC, CD, and DE, named for the helices they connect. Helices A and B are parallel to each other, but the remaining helices run antiparallel to each adjacent helix (Radhakrishnan, 1999). These designations vary slightly from those of IFN-β. The greatest divergence between the different IFNs occurs in the loop regions and the amino terminus.

Despite the overall structural similarity between the type I IFNs, significant differences also exist. The greatest variations occur at the N-terminus (aa 6–7), helix A and the AB1 loop (aa 23–32), the AB3 loop (aa 49–52), helix B and the BC loop (aa 71–77). These regions are located on one face of the molecule and are thought to be directly involved in receptor binding.

IFNs must interact with their cell surface receptors in order to elicit a response. There are two types of IFN receptors, one that interacts with the type I IFNs and one that interacts with type II IFNs (Mariano, 1992). Both receptor types are transmembrane proteins in the type II family of cytokine receptors. Not all type I IFNs bind similarly to all cellular receptors. IFN-α binds the type I receptor with a much greater affinity than does IFN-τ; this greater binding affinity was associated with maximal receptor occupancy. This increased occupancy has been further associated with increased toxicity. This relationship is one possible explanation for the decreased cytotoxicity seen with IFN-τ.

Previous mutagenesis studies on IFN-tau have focused on the C-terminus (18). Deletion of the C-terminal 11 residues significantly decreased antiviral and antiproliferative activity, but had only a slight negative effect on receptor binding. An 11 amino acid C-terminal truncation and substitution at lysine 160 did not produce large changes in endometrial membrane receptor binding, but eliminate antiviral activity and reduce antiproliferative activity on human cell lines. The same study also showed that replacement of isoleucine with threonine in helix E significantly lowered receptor binding affinity by 95%, reduced antiviral activity by 87%, and abolished antiproliferative activity completely. Li, ,J., *The Journal of Biological Chemistry*, 269:40, 24826–24833(1994).

Extensive structure function studies have been performed on the type I IFNs, to identify the relationship between the conformation of the molecule and activity. Studies of synthetic peptides revealed that segments spanning amino acids 1–37, 62–92 and 139–172 on the IFN-τ molecule that are important for antiviral activity (Pontzer, C., *Journal of Interferon Research* 14, 133–41 (1994). This data indicates that the amino and carboxyl termini are both important for receptor binding and corresponds with the 3-dimensional structure of IFN-τ, which shows that amino and carboxyl termini are physically in close proximity (14).

The potency of various IFNs has been suggested to be related to receptor binding affinity (25). Differential receptor binding may play a significant role in the different biological properties of type I IFNs. Previous structure-function studies on IFN-alpha and IFN-tau support the working hypothesis that these regions are important for interferon activity.

Extensive mutagenesis studies have pointed to loop AB as one of the "hot spots" for receptor binding and biological function (15). Mutations of human IFN-beta and IFN-alpha at positions 27 and 35, as well as at position 123 have been shown to reduce antiviral activity (16). Studies using peptides corresponding to various regions of IFN-tau have shown that residues 1–37 inhibit the antiviral activity of ovine IFN-tau on MDBK cells, but do not compete with huIFN-alpha2 to inhibit its activity (17). The amino termini of IFN-α and IFN-τ show the greatest sequence dissimilarity and the greatest divergence in structure (14); previous structure-function studies on IFN-α and IFN-β strongly suggest that these regions are important for interferon activity. It has been suggested that the N-terminus of IFN-τ interacts with the type I IFN receptor in a distinct manner and is responsible for some of IFN-τ's unique activity (8,17).

B. Selection and Design of the Interferon Mutants Having Improved Biological Activity While previous studies showed site directed mutations in the carboxyl terminus had virtually no effect on antiviral or antiproliferative activity (Li, 1994), it has now been discovered that certain carefully selected, single, biologically directed substitutions in the amino-terminal region of ovine IFN-tau1mod unexpectedly increased antiproliferative activity of the corresponding mutant proteins on human cells while retaining antiviral activity, without increasing cytotoxicity, as will be discussed below.

The examples below focus on six nonconserved residues within the N-terminus. The experimental strategy involved changing particular nonconserved amino acids in the well characterized native ovine IFN-τ 1mod which has AMINO ACID SEQ. ID NO. 2, and NUCLEIC ACID SEQ. ID NO. 1 to those in corresponding positions in human interferon alpha A (IFN-αA) which has AMINO ACID SEQ. ID NO.3. Changing the structure of ovine IFN-τ 1mod one amino acid at a time facilitated the assessment of the contribution of individual amino acids to IFN-τ activity, as well as a comparison to see if substitution of any of the residues created a mutant interferon tau with increased antiviral or antiproliferative activity more like that of human IFN-αA. Similar observations can be made by substituting more than one amino acid residue at a time to make these comparisons to interferon alpha. Likewise, similar site-directed mutations can be made to compare the structure and/or biological activity of other mutants compared to any reference molecule. For example, ovIFN-τ1mod can be mutated with reference to structurally similar regions of interferon beta or interferon omega and other alpha interferons.

Such mutants have clinically significant therapeutic uses in the treatment of a wide range of cancers and immune diseases including autoimmune diseases, that have been shown in previous studies to respond to treatment by interferon tau, interferon alpha, interferon beta and other interferons having structural similarity to the interferon tau 1mod mutants of the present invention, because it is clearly preferable to use an interferon that has the desired biological activity without cytotoxicity.

Six mutants of IFN-tau1mod have been constructed. It was decided to select for substitution, those amino acids in the N terminal region of native ovine IFN-tau that are exposed to solvent AND that differ from the corresponding solvent-exposed amino acid on human Interferon alpha. Those amino acids in the N-terminal region of each molecule that were exposed to solvent were identified based on the structure (predicted or crystallized structure). The amino acids exposed to solvent were compared and the amino acids in this group that were different between interferon tau and alpha were identified. Six mutations were made in interferon tau, one amino acid at a time, chosen from the solvent-exposed amino acids that were different between IFN-tau and IFN-alpha. The mutations were created using site directed mutagenesis to specifically convert one specific amino acid in ovine IFN-τ1mod to the amino at the corresponding position in human IFNαA by changing the DNA codon. Other methods of making the appropriate DNA for the tau mutants known to those skilled in the art can be used. Three mutations were at sites within helix A and three within the AB loop where the solvent exposed amino acid sequence of ovine IFN-τ1mod was shown to differ from to the amino acid at the corresponding position in human IFNαA.

The mutations identified by their amino acid sequences are:

| | |
|---|---|
| THE 13 E:R MUTANT | AMMINO ACID SEQ. ID NO. 4, NUCLEIC ACID SEQ. ID NO. 11, |
| THE 16 K:M MUTANT, | AMMINO ACID SEQ. ID NO. 5, NUCLEIC ACID SEQ. ID NO. 12 |
| THE 19 D:A MUTANT | AMMINO ACID SEQ. ID NO. 6, NUCLEIC ACID SEQ. ID NO. 13, |

| | |
|---|---|
| THE 24 L:I MUTANT | AMINO ACID SEQ. ID NO. 7; NUCLEIC ACID SEQ. ID NO. 14 |
| THE 26 P:L MUTANT | AMINO ACID SEQ. ID NO. 8, NUCLEIC ACID SEQ. ID NO. 15; |
| THE 31 Q:K MUTANT | AMINO ACID SEQ. ID NO. 9, NUCLEIC ACID SEQ. ID NO. 16; and |
| THE 34 K:H MUTANT | AMINO ACID SEQ. ID NO. 10, NUCLEIC ACID SEQ. ID NO. 17 |
| THE 5 R:Q MUTANT | AMINO ACID SEQ. ID NO. 18, |
| THE 6 K:T MUTANT | AMINO ACID SEQ. ID NO. 19, |
| THE 20 R:Q MUTANT | AMINO ACID SEQ. ID NO. 20, |

It is important to emphasize that due to redundancy in the genetic code, the nucleic acid sequences set forth above are only one of many nucleic acid sequences for each respective mutant. Other IFN-tau mutants that were identified but not made are 5 R:Q which has the same amino acid sequence as native ovine IFN-tau1mod in SEQ. ID No. 2, except for having a glycine (GLN) residue instead of an arginine (ARG) at position 5; 6 K:T which has the same amino acid sequence as native ovine IFN-tau1mod in SEQ. ID No. 2, except for having a threonine residue instead of a lysine at position 6; and 20 R:Q which has the same amino acid sequence as native ovine IFN-tau1mod in SEQ. ID No. 2, except for having a glycine residue instead of an arginine at position 20. The 5, 6 and 20 IFN-tau mutants also come within the present invention.

Specific residues within helix A and the AB loop that affect antiproliferative and/or antiviral activity were identified by testing each mutated IFN-tau. Antiproliferative and/or antiviral activity were not equally affected by the six particular mutations as is discussed below. Changes in antiproliferative activity were cell type specific. Thus this invention includes designing novel proteins to specifically target a type of normal or malignant cell. Normal cells to be targeted include but are not limited to inflammatory cells, sex cells, or any excessively dividing or excessively functioning cells. One mutant, 26P:L, displayed both antiviral and antiproliferative potency equivalent to that of the human IFN-α, while maintaining the lack of in vitro cytotoxicity of ovine IFN-τ1mod. None of the N-terminal mutants examined had altered cytotoxicity profiles, suggesting that these mutants have superior therapeutic activity.

The present invention includes the IFN-tau mutants described above, but further includes any substitutions into the mutant selected from differing amino acids in any region of interferon alpha or other type 1 interferon including interferon beta or omega. The present invention further includes as a region of biological activity, any binding sites and other regions of a molecule that are involved in proper folding or structural integrity of the molecule, or receptor binding or activation.

C. Recombinant Production of Interferon Tau Mutants

Recombinant OvineIFNt1mod mutant proteins were produced using bacterial and yeast cells. Details are set forth in Example 1.

Construction of ovineIFN-tau1mod Mutagenesis/Expression vector

For construction of the ovIFN-tau1mod mutagenesis/expression vector, the gene for ovIFN-□1mod was amplified by PCR using Taq polymerase (Stratagene, La Jolla, Calif.) and cloned into the E. coli vector pCR2.1 (Stratagene TA cloning kit) before ultimately being cloned into the Kpn I site of the E. coli-yeast shuttle vector pPICZ alpha (Invitrogen). [Example 1].

For expression of recombinant interferon polypeptides, the chimeric coding sequence can be placed in a number of bacterial expression vectors: for example, lambda gt11 (Promega, Madison, Wis.); pGEX (Smith, D. B., et al., 1988); pGEMEX (Promega); and pBS (Stratagene, La Jolla, Calif.) vectors. Other bacterial expression vectors containing suitable promoters, such as the T7RNA polymerase promoter or the tac promoter, may also be used. Cloning of the Ovine IFN-tau. polynucleotide into a modified pIN III omp-A expression vector is also possible.

Other yeast vectors can be used in the practice of the present invention. They include 2 micron plasmid vectors, yeast integrating plasmids, YEP vectors, yeast centromere plasmids, and the like known to those skilled in the art. The AOX promoter is particularly useful in Pichia pastoris host cells (for example, the AOX promoter is used in pHIL and pPIC vectors included in the Pichia expression kit, available from Invitrogen, San Diego, Calif.).

Additional yeast vectors suitable for use with the present invention include, but are not limited to, other vectors with regulatable expression. The yeast transformation host is typically Saccharomyces cerevisiae, however, other yeast suitable for transformation can be used as well (e.g., Schizosaccharomyces pombe, Pichia pastoris and the like.

The DNA encoding the IFN-tau. polypeptide can be cloned into any number of commercially available vectors to generate expression of the polypeptide in the appropriate host system. These systems include the following: baculovirus expression; plant cell expression, transgenic plant, and expression in mammalian cells (Clontech, Palo Alto Calif.; Gibco-BRL, Gaithersburg Md.). A number of features can be engineered into the expression vectors, such as leader sequences, which promote the secretion of the expressed sequences into culture medium. The recombinantly produced polypeptides are typically isolated from lysed cells or culture media purification can be carried out by methods known in the art including salt fractionation, ion exchange chromatography, and affinity chromatography. Immunoaffinity chromatography can be employed using antibodies generated based on the IFN-tau. polypeptides.

Site-Directed Mutagenesis is one way to introduce the necessary mutations into ovine IFN-tau1mod DNA to effect the requisite amino acid substitutions. Other methods are known to those skilled in the art. Six mutations were introduced using the Quickchange Site Directed Mutagenesis kit (Stratagene) following manufacturers instructions. Briefly, primers containing the desired base changes were synthesized by Bioserve (Laurel, Md.) or Integrated DNA Technologies (Coralville, Iowa). They were added to 50–100 ng of pPICZalpha containing the gene for ovIFN-tau1mod with Pfu turbo polymerase (Stratagene) in a 50 micro liters reaction and cycled to incorporate the desired base change(s). Each reaction was optimized for each set of primers. Five micro liters of the PCR reaction was run on a 1% agarose gel to visualize the product. The remaining reaction was digested with Dpn I for 1 hour, purified, and used to transform XL-1 Blue Ultracompetent cells (Stratagene). Transformants were selected on low salt LB in the presence of zeocin (Invitrogen). Plasmid DNA from transformants was extracted with phenol-chloroform and ethanol precipitated. The incorporation of the correct mutations was verified by dideoxy sequencing.

Production of Mutant IFN-tau Proteins in P. pastoris-E. coli

Mutant IFN-tau proteins were produced in P. pastoris-E. coli carrying the recombinant plasmid. Plasmid DNA was linearized and used to transform P. pastoris. Yeast colonies containing the desired gene were selected and grown. Proteins were secreted into the media and purified by ammonium sulfate precipitation and anion exchange column chromatography. The concentration of IFN-tau and mutant IFN-tau proteins was measured using the BCA protein assay (Pierce). The protein can be further purified by standard methods, including size fractionation (column chromatography or preoperative gel electrophoresis) or affinity chromatography (using, for example, anti-ovine IFN-tau. antibodies (solid support available from Pharmacia, Piscataway N.J.). Protein preparations can also be concentrated by, for example, (Amicon, Danvets, Mass.), HPLC, capillary electrophoresis or other protein purification methods known or that may become known may be used. Purified proteins were analyzed using Ovine IFN-tau1mod Mutant Protein Immunoblots. All of the immunoblots had a single 19 KD band indicating the production of a 172 amino acid protein.

E. Toxicity of the Interferon Tau Mutants

Viability of IFN-tau Mutant-Treated Cells-As has previously been shown with peripheral blood lymphocytes, U937 cells exhibited significantly reduced viability when treated with human IFN-alpha A as compared with ovine IFN-tau1mod. All of the IFN-tau mutant proteins exhibited low in vitro cytotoxicity profiles similar to that of the parental ovIFN-tau1mod that suggests this region may not be involved in the reduced cytotoxicity of ovine IFN-tau1mod. Because all of the mutants showed roughly the same low toxicity profile of unmodified ovIFN-tau1mod, and because the point mutations were all in the N-terminal region of the molecule, the results suggest that this region is probably not involved in the reduced cytotoxicity of ovine IFN-tau1mod, rather it affects potency.

F. Antiproliferative Activity of Interferon Tau Mutants

The ability of IFNs to decrease cell proliferation is an important and well documented phenomenon that has been tested in many human and animal cell lines. The various mutants to ovine IFN-t1mod in the N-terminal region had cell type-specific effects on antiproliferative activity. Nonetheless, each of the mutants maintained equivalent antiproliferative activity relative to the parental IFN-τ on at least one cell line. Antiproliferative activity was measured on two adherent cell lines, MCF-7 (breast adenocarcinoma) and HT-29 (colon adenocarcinoma), and one suspension cell line, Daudi (Burkitt lymphoma). Antiproliferative activity is measured as the percent of cells grown in the presence of IFN divided by the number of cells grown in the absence of IFN. It is understood that testing mutant proteins made according to the present invention involves only routine screening against various known cell lines, or cell lines established for any given patient, using methods known to those skilled in the art.

Thirty-three units of ovIFN-τ1mod (0.06 nM) caused a 54% decrease in proliferation of Daudi cells. IFN-α caused an even greater decrease in proliferation of 69%. Four of the mutants were tested on Daudi cells. These are 13 E:R, 16 K:M, 26 P:L, and 34 K:H. Importantly, all four of these tau mutants reduced the cell numbers as well as, or better, than did ovIFN-τ1mod with the 26P:L mutant exhibiting the greatest antiproliferative activity. This mutant caused an 81% decrease in cell number as compared to cells in media alone, an activity profile similar to that of the IFNα without the cytotoxicity, which gives the 26 tau mutant a high therapeutic index for treating cancer and tumors.

The 16 K:M and 34K:H mutants also produced statistically significant decreases in tumor cell proliferation indicating that they had statistically significant increases in antiproliferative activity compared to native IFN-tau, making them also clinically useful anticancer and antitumor agents with a high therapeutic index. Both the 16 and 34 mutants were significantly more effective than native IFN τ and nearly as effective as IFNα without the toxicity.

Two additional adherent cell lines, HT-29 and MCF-7, were used to test the same property. These cell lines are not as sensitive to type I IFNs and required much higher doses to inhibit cell growth. All but one of the mutants significantly decreased cell number of HT-29 cells compared to control. The 26 P:L mutation significantly increased antiproliferative activity relative to wildtype IFN-τ, again without increasing cytotoxicity, suggesting that this position contributes to overall function of IFN-τ.

All of the mutants inhibited proliferation of MCF-7 cells compared to controls; however, the activity of the mutants did not significantly differ from that of ovine IFN-τ1mod. As seen previously, the IFN-τ 26P:L mutant had the greatest antiproliferative activity.

G. Binding of the Interferon Tau Mutants to Type I Receptor

Binding to the Type I IFN Receptor-Binding of $^{125}$I-ovIFN 1mod to the common type I IFN receptor was most efficiently displaced by human IFÑαA (FIG. 1). OvIFN-τ1mod itself produced only half of the displacement seen with the IFÑα. The majority of the AMINO ACID substitutions introduced to create the IFN-τ mutants decreased the ability of the mutant proteins to displace the labeled ovIFN-τ1mod; this decrease was statistically significant with the 24L:1 and 34K:H mutants. By contrast, the P:L substitution at residue 26 significantly increased competition of labeled ovIFN-τ1mod binding, though still not to the same extent as did the human IFN-αA.

The potency of various IFNs has been suggested to be related to receptor binding affinity (25). The reduced antiproliferative potency and reduced toxicity of ovIFN-τ1mod relative to human IFÑτ on MDBK cells has been seen as a reflection of Kd, $3.90 \times 10^{-10}$ and $4.45 \times 10^{-11}$ for IFN-τ and α, respectively (8). Hence, the enhanced receptor binding of the IFN-τ 26 P:L mutant relative to the parental IFN-τ may be predictive of enhanced biological activity or potency.

H. Antiviral Properties of the Interferon Tau Mutants

The antiviral activity of the six IFN-t mutants was measured using a standard cytopathic effect inhibition assay using MDBK cells and vesicular stomatitis virus (VSV; 22). Antiviral activity was normalized based on the reference IFN-alpha Gxa01-901-535. One unit of antiviral activity is defined as the amount of protein needed to inhibit the cytopathic effect of VSV by 50%. All the mutants possessed antiviral activity to some extent. The activity of the IFN-t 26P:L mutant was $9.5 \times 10^7$ U/mg, which is as great as that of both ovine IFN-tau1mod and IFN-alpha.

The activity of four other mutants, 16K:M, 19D:A, 24L:I, and 34K:H, exhibited significantly reduced the antiviral activity relative to the parental IFNτ controls. The least active mutant was 13E:R, having $3.2 \times 10^4$ U/mg.

In a preferred embodiment, the IFN-t 26P:L mutant having improved antiviral activity is administered in therapeutically effective amounts to treat viral infections, including, hepatitis B and C, genital warts, cytomegalovirus infections.

The present invention is not limited to amino acids substitutions in the first protein that increase antiproliferative or antiviral activity but include any substitutions that improve any measurable biological activity, such as improved receptor binding, decreased toxicity, improved molecular stability, or improved affinity for antibodies. The improved biological activity may be decreased receptor binding in some circumstances.

I. Utility

A. Reproductive

Although IFN-tau. bears some similarity to the IFN-alpha. family based on structure and its potent antiviral properties, the IFN-alphas- do not possess the reproductive properties associated with IFN-tau. For example, recombinant human IFN-alpha. had no effect on interestrous interval compared to IFN-tau., even when administered at twice the dose (Davis, et al., 1992).

Therefore, although IFN-tau. has some structural similarities to other interferons, it has very distinctive properties of its own: for example, the capability of significantly influencing the biochemical events of the estrous cycle.

The IFN-tau. mutants of the present invention can be used in methods of enhancing fertility and prolonging the life span of the corpus luteum in female mammals as generally described in Hansen, et al., 1991, herein incorporated by reference. Further, the mutants of the present invention could be used to regulate growth and development of uterine and/or fetal-placental tissues in animals. Mutants may also be used as contraceptives in animals.

B. Antiviral Agent

Type I interferons exhibit potent antiviral properties. The antiviral activity of native IFN-tau. has broad therapeutic applications without the toxic effects that are usually associated with IFN-alphas. The IFN-tau mutants of the present invention were found to exert their antiviral activity without adverse toxic effects on human cell lines. This lack of cytotoxicity sets IFN-tau and these mutant IFN-tau proteins apart from most other known antiviral agents and all other known interferons. Formulations comprising the IFN-tau.mutants of the present invention can therefore be used to treat or prevent viral infections, including hepatitis B and C, AIDS, meningitis, TB, hepatitis B and C, HIV, cutaneous viral infections (chickenpox, herpes zoster, measles), respiratory viral infections, viral diseases of the central nervous system, viral diseases of the liver, viral diseases of the salivary glands, infectious mononucleosis, and genital warts. Since interferons increase macrophage activity, they may also be useful in the treatment of additional bacterial, fungal and parasitic diseases.

The IFN-tau mutants are especially useful against human papillomavirus infection, Hepatitis B, and Hepatitis C infections where interferon alpha, which binds to the same receptor as IFN-tau, is known to be effective. (Finter, et al., 1991; Kashima, et al., (*Laryngoscope* 98:334(1988); Dusheiko, et al. *J. Hematology* 3 (suppl.2):S199(1986); Davis, et al., *N. England J. Med.* 321:1501(1989). The journal articles listed in this application are all incorporated in their entirety.

C. Anticellular Proliferation Properties

Type I interferons exhibit potent anticellular proliferation activity. The IFN-τ mutants described herein can also be used to inhibit cellular growth without the negative side effects associated with other interferons. Formulations comprising the mutant interferon-τ compounds of the subject invention can be used to inhibit, prevent, or slow tumor or cancer growth.

The development of certain tumors is mediated by estrogen. Previous studies show that IFN-tau. can suppress estrogen receptor numbers. U.S. Pat. No. 5,939,286. Therefore, IFN-tau mutant-containing compositions can also be used in the treatment or prevention of estrogen-dependent tumors.

The antiproliferative properties of IFN-tau mutants together with its low toxicity make it useful in the treatment of cancer, malignant tumors, and precancerous tumors. As to neoplasia treatment, the compounds of the invention can be used to treat a variety of preneoplastic and neoplastic conditions, including both soft (e.g. hematolymphoid) and solid tumors (e.g. carcinomas and sarcomas). More specifically, the compounds of the invention can be used to treat breast cancer, prostate cancer, glioblastomas, melanomas, myelomas, lymphomas, leukemias, lung cancer, skin cancer, bladder cancer, kidney cancer, brain cancer, ovarian cancer, pancreatic cancer, uterine cancer, bone cancer, colorectal cancer, cervical cancer and neuroectodermal cancer, and premalignant conditions, including, without limitation, monoclonal gammapothies, dysplasia, including, without limitation, cervical and oral dysplasia. Interferons are known to be especially effective in the treatment of hairy-cell leukemia (Quesada, J. R. et al., *N. England J. Med.* 310:15 (1984). Further, these proteins have also shown activity against multiple myeloma, chronic lymphocytic leukemia, low-grade lymphoma, chronic myelogenous leukemia, renal-cell carcinoma, urinary bladder tumors, and ovarian cancers.

The interferon-tau mutants are especially useful in treating Kaposi's sarcoma, non-Hodgkin's lymphoma and malignant melanoma (Mariano, T. M., *Interferons: Principles and Medical Applications*, 1992, 129–138(1992), chronic myelogenous leukemia, cutaneous squamous cell carcinoma, and laryngeal papillomatosis.

Other cancers that can be treated with the mutants of the present invention include ocular-retinoblastoma, intraocular melanoma, oropharyngeal, paranasl sinus and nasal cancers, hypopharyngeal, laryngeal, salivary gland, occult primaray mesotelioma (Squamous Cell), Non-Small Cell Lung cancer, Small-Cell Lung cancer, Maligant Thymoma, Maligant Mesthelioma, Esophageal cancer, Gastric cancer, Primary Live cancer, Intrahepatic Bile Duct cancer, Extrahepatic Bile Duct cancer, and cancers of the Gallbladder, Pancreatic, Small Intestine, Gastrointestinal Carcinoid, Colon, Rectal, Anal Canal & Anus, Renal Cell, Transitional Cell of Renal Pelvis and Ureter, Bladder, Urethral, Prostate, Penile, Testicular, Extragonadal & Gonadal Germ Cell Tumors, Ovarian Epithelial, Ovarian Low Malignant Potential Tumor, Ovarian Germ Cell, Endometrial, Uterine Sarcoma, Gestational Trophoblastic, Cervical, Vaginal, Vulvar, Melanoma, Skin, Adult Soft Tissue Sarcoma, Endroctrine including Thyroid, Islet Cell Neoplasia, Adrencortical, Phechromocytoma, Carcinoma of Unknown Primary origin, Hematolgic Neoplasms including Acute Myeliod, Chronic Myelogenous, Hairy Cell, and Hodgkin's.

D. Immune System Disorders

Diseases which may be treated using methods of the present invention include autoimmune, inflammatory, proliferative and hyperproliferative diseases, as well as cutaneous manifestations of immunologically mediated diseases. In particular, methods of the present invention are advantageous for treating conditions relating to immune system hypersensitivity. There are four types of immune system hypersensitivity. Type I, or immediate/anaphylactic hypersensitivity, is due to mast cell degranulation in response to an allergen (e.g., pollen), and includes asthma, allergic rhinitis (hay fever), urticaria (hives), anaphylactic shock, and other illnesses of an allergic nature. Type II, or autoimmune hypersensitivity, is due to antibodies that are directed against perceived "antigens" on the body's own cells. Type III hypersensitivity is due to the formation of antigen/antibody immune complexes which lodge in various tissues and activate further immune responses, and is responsible for conditions such as serum sickness, allergic alveolitis, and the large swellings that sometimes form after booster vaccinations. Type IV hypersensitivity is due to the release of lymphokines from sensitized T-cells, which results in an inflammatory reaction. Examples include contact dermatitis, the rash of measles, and "allergic" reactions to certain drugs.

Autoimmune diseases that can be treated with the IFN-τ mutants include but are not limited to, multiple sclerosis, systemic lupus erythematosus, and type I diabetes mellitus, alone or in conjunction with other treatments known to be effective in treating auto-immune diseases, including, but not limited to, corticosteroids. Additionally the IFN-τ mutants may be used to prevent graft-versus-host reactions, both alone and in combination with other pharmaceutical preparations known to be useful in preventing graft-versus-host reactions, including, but not limited to, cyclosporine and corticosteroids.

Autoimmune disorders may be loosely grouped into those primarily restricted to specific organs or tissues and those that affect the entire body. Examples of organ-specific disorders (with the organ affected) include multiple sclerosis (myelin coating on nerve processes), type I diabetes mellitus (pancreas), Hashimotos thyroiditis (thyroid gland), pernicious anemia (stomach), Addison's disease (adrenal glands), myasthenia gravis (acetylcholine receptors at neuromuscular junction), rheumatoid arthritis (joint lining), uveitis (eye), psoriasis (skin), Guillain-Barre Syndrome (nerve cells) and Grave's disease (thyroid). Systemic autoimmune diseases include systemic lupus erythematosus and dermatomyositis.

Other examples of hypersensitivity disorders include asthma, eczema, atopical dermatitis, contact dermatitis, other eczematous dermatitides, seborrheic dermatitis, rhinitis, Lichen planus, Pemplugus, bullous Pemphigoid, Epidermolysis bullosa, uritcaris, angioedemas, vasculitides, erythemas, cutaneous eosinophilias, Alopecia areata, atherosclerosis, primary biliary cirrhosis and nephrotic syndrome. Related diseases include intestinal inflammations, such as Coeliac disease, proctitis, eosinophilia gastroenteritis, mastocytosis, inflammatory bowel disease, Chrohn's disease and ulcerative colitis, as well as food-related allergies.

Autoimmune diseases particularly amenable for treatment using the methods of the present invention include multiple sclerosis, type I (insulin dependent) diabetes mellitus, lupus erythematosus, amyotrophic lateral sclerosis, connective tissue diseases, Chrohn's disease, rheumatoid arthritis, stomatitis, asthma, uveitis, allergies and psoriasis.

E. Pharmaceutical Compositions.

IFN-tau mutant of the present invention may be co-administered with more toxic interferons to reduce the toxicity of the more toxic interferons when used in pharmaceutical formulations or in therapeutic applications. Such IFN-tau mutants would, for example, reduce the toxicity of IFN-alpha but not interfere with IFN-alpha. antiviral properties. IFN-τ mutants may be administered enterally (oral administration) or mucosally (including eye, nose, mouth, vagina and rectum), parentally in suitable pharmaceutical compositions known to those skilled in the art and described in the medical literature. The mutants may be combined with agents to allow dermal or mucosal penetration.

IFN-tau mutant proteins can be formulated according to known methods for preparing pharmaceutically useful compositions. Formulations comprising interferons or interferon-like compounds have been previously described (for example, Martin, 1976). In general, the compositions of the subject invention will be formulated such that an effective amount of the IFN-tau. is combined with a suitable carrier in order to facilitate effective administration of the composition.

The compositions used in these therapies may also be in a variety of forms. These include, for example, solid, semi-solid, and liquid dosage forms, such as tablets, pills, powders, liquid solutions or suspensions, liposomes, emulsions, microemulsions, suppositories, injectable, and infusible solutions or other methods known or developed to administer proteins. The IFN-tau mutants can also be conjugated with polyethylene glycol or other polymers or agents to reduce toxicity or improve pharmacokinetics or pharmacologic properties. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

IFN-tau mutants may be administered to a patient in any pharmaceutically acceptable dosage form, including oral intake, inhalation, intranasal spray, intraperitoneal, intravenous, intramuscular, intralesional, or subcutaneous injection. Specifically, compositions and methods used for other interferon compounds can be used for the delivery of these compounds.

One primary advantage of the compounds of the subject invention, however, is the extremely low cytotoxicity of the IFN-tau mutants. Because of this low cytotoxicity, it is possible to administer the IFN-tau mutants. in concentrations which are greater than those which can generally be utilized for other interferon (e.g., IFN-alpha.) compounds. Thus, IFN-tau mutants. can be administered at rates from about 5.times. 10.sup.4 to 20.times. 10.sup.6 units/day to about 500.times. 10.sup.6 units/day or more. In a preferred embodiment, the dosage is about 20.times. 10.sup.6 units/day. High doses are preferred for systemic administration. It should, of course, be understood that the compositions and methods of this invention may be used in combination with other therapies. Further, the effective dose varies from disease to disease and patient to patient, and the optimum dose and administration schedule can be determined by methods known to those skilled in the art.

Once improvement of a patient's condition has occurred, a maintenance dose is administered if necessary. Subsequently, the dosage or the frequency of administration, or both, may be reduced, as a function of the symptoms, to a level at which the improved condition is retained. When the symptoms have been alleviated to the desired level, treatment may cease if recurrence of symptoms does not occur. Patients may, however, require intermittent treatment on a long-term basis upon any recurrence of disease symptoms.

The compositions of the subject invention can be administered through standard procedures to treat a variety of cancers and viral diseases including those for which other interferons have previously shown activity. See, for example, Finter, et al., *Drugs* 42(5): 749(1991); Dianzani, et al., *Interferon Res., Special Issue*, 5/92:109(1992); Francis, et al., *AIDS Res. And Human Retroviruses* 8(2):199(1992) and U.S. Pat. Nos. 4,885,166 and 4,975,276. However, as discussed above, the compositions of the subject invention have unique features and advantages, including their ability to treat these conditions without toxicity.

F. Treatment of Skin Disorders.

Disorders of the skin can be treated intralesionally using IFN-tau mutants, wherein formulation and dose will depend on the method of administration and on the size and severity of the lesion to be treated. Preferred methods include intradermal and subcutaneous injection or local application in a variety of vehicles. Multiple injections into large lesions may be possible, and several lesions on the skin of a single patient may be treated at one time. The schedule for administration can be determined by a person skilled in the art. Formulations designed for sustained release can reduce the frequency of administration.

G. Systemic Treatment.

Multiple intravenous, subcutaneous and/or intramuscular doses are possible, and in the case of implantable methods for treatment, formulations designed for sustained release are particularly useful. Patients may also be treated using implantable subcutaneous portals, reservoirs, or pumps.

H. Regional Treatment.

Regional treatment with the IFN-tau mutants of the present invention are useful for treatment of cancers in specific organs. Treatment can be accomplished by intraarterial infusion. A catheter can be surgically or angiographically implanted to direct treatment to the affected organ. A subcutaneous portal, connected to the catheter, can be used for chronic treatment, or an implantable, refillable pump may also be employed.

I. Veterinary Diseases

The IFN-tau mutants can be used in veterinary applications wherever other interferons are used, including, but not limited to, the treatment of the following viral diseases: feline leukemia virus, ovine progressive pneumonia virus, ovine lentivirus, equine infectious anemia virus, bovine immunodeficiency virus, visnamaedi virus, and caprine arthritis encephalitis.

Various aspects of the present invention are described in greater detail in the non-limiting Examples that follow.

EXAMPLE I

Materials & Methods

Bacterial and Yeast Strains

The *Escherichia coli* strains used were DH5α and XL-1 (Stratagene) and INVαF (Stratagene). *Pichia pastoris* strain SMD1168 was used. The IFN-τ gene was amplified from a *Pichia pastoris* construct in strain GS115.

Media Bacterial media was LB (10 g bacto-tryptone (Difco), 5 g bacto-yeast extract (Difco) and 10 g NaCl (Sigma) in 950 mL of water, supplemented with 15 g agar (Fisher) for plates) or low-salt LB (same as LB but with 5 g NaCl instead of 10 g). Antibiotics were added at a concentration of 60 µg/mL for ampicillin (Sigma), 50 g/mL for kanamycin (Sigma) or 50 µg/mL for zeocin (Invitrogen).

Yeast media was YPD (1% yeast extract, 2% peptone (Difco), 2% dextrose (J. T. Baker), supplemented with 2% agar for plates), BMGY (1% yeast extract, 2% peptone, 100 mM potassium phosphate, pH 6.0 (Fisher), 1.34% Yeast Nitrogen Base (Difco), $4 \times 10^{-5}$% Biotin (Sigma), 1% glycerol (Fisher), supplemented with 2% agar for plates), BMMY (same as BMGY but with 0.5% methanol (Fisher) instead of glycerol). Zeocin was added to yeast media at a concentration of 100 µg/mL.

Cell Lines- MDBK cells were cultured in minimal essential media (MEM) with 10% fetal bovine serum (FBS) and antibiotics. All the human tumor cell lines were obtained from ATCC (Rockville, Md.). MCF-7 cells were grown in Eagle's MEM with 1 mM sodium pyruvate, L-glutamine, antibiotics and 10% FBS. HT-29 cells were grown in Eagle's MEM supplemented with 0.1 mM non-essential amino acids, 1 mM sodium pyruvate, 10 pg/ml bovine insulin, L-glutamine, antibiotics and 10% FBS. Daudi cells were grown in RPMI 1640 containing 20% FBS.

Interferons—The gene encoding ovIFN-tau1mod has been cloned into the methyltropic yeast *Pichia pastoris* (Invitrogen, San Diego, Calif.) under the control of the alcohol oxidase promoter (19). Upon induction with methanol, ovIFN-tau1mod is produced as a secreted protein. It was purified by ammonium sulfate precipitation followed by anion exchange chromatography using diethylaminoethyl cellulose (Sigma, St. Louis, Mo.). The specific activity of the purified protein was $1 \times 10^8$ units/mg. Recombinant human IFN-alphaA was purchased from Intergen (Purchase, N.Y.) and PBL (New Brunswick, N.J.) with specific activities of $3 \times 10^8$ units/mg and $1 \times 10^8$ units/mg, respectively.

Construction of ovine IFN-□1mod Mutagenesis/Expression vector—For construction of the ovIFN-tau 1mod mutagenesis/expression vector, the gene for ovIFN-tau 1mod was amplified by PCR using Taq polymerase (Stratagene, La Jolla, Calif.) and cloned into the *E. coli* vector pCR2.1 (Stratagene TA cloning kit) before ultimately being cloned into the Kpn I site of the *E. coli*-yeast shuttle vector pPICZalpha (Invitrogen).

Amplification of the Gene for IFN-τ from Yeast

The IFN-τ 1mod gene was amplified directly from the yeast genome of *Pichia pastoris*. The genomic DNA was prepared directly for PCR from a colony, following a protocol in Biotechniques (Ward, 1996).

Amplification of the gene was accomplished by PCR. New restriction sites were added to the primers because the original gene in yeast has no restriction sites due to their loss during a double recombination event (Ott, 1991).

Use of pPICZα Vector

Another vector was also used, the pPICZα vector from Invitrogen. Different primers were required. The primers were:

Primer 1 (identical to the 5'-end of coding strand with a KpnI (GGTACC) and SnaBI (TACGTA) sites added, indicated by underlining)

5'-TA<u>GGTACC</u>AC<u>TACGTA</u>GCGTGCTACCTGTCG-3'

Primer 2 (identical to the 3'-end of non-coding strand with overlapping kpnI (GGTACC) and SacII (CCGCGG) sites added, indicated by underlining)

5'-TA<u>GGTACCGCGG</u>TTACGGAGAATTCAGG-3'

Genomic DNA can be used as template for the PCR reaction with the high fidelity polymerase, PFU (Stratagene). Another method to accomplish taking the mutant tau gene taken out of the yeast gene and putting it into a vector, involves taking the genomic DNA, amplifying it with PCR and then putting the amplified gene into the PCR2.1 *E. coli* vector, and from PCR2.1 into pPICZ alpha vector. PCR2.1 uses a different set of primers.

The PCR product was visualized on agarose gel electrophoresis and purified using GENECLEAN®. The PCR product was then digested with KpnI (Promega), as was the vector pPICZα. Double digested vector was visualized on agarose gel electrophoresis, cut out and purified using GENECLEAN® and dephosphorylated using alkaline phosphatase (as above). The insert and vector were ligated as per directions from the Rapid DNA Ligation Kit. Half the ligation mix was transformed into 130 µL of XL-1 Blue Ultracompetent *E. coli*. Transformants were selected for on low salt LB plates with zeocin (Invitrogen). Clones were identified by size and then by digestion with HindIII (Promega) to check for orientation. The constructs in pPICZα contained DNA encoding seven extra amino acids at the 5'-end of inserted gene. These amino acids were deleted by digesting first with PmlI (New England Biolabs) at 37° C. overnight. The PmlI digests were then visualized on an agarose gel, excised, and purified using GENECLEAN®. The purified DNA sample was then digested with SnaBI. The blunt ends were then ligated together to recircularize the plasmid using the Rapid DNA Ligation Kit, per the supplied protocol. Half of the ligation mix (10 μL) was then transformed into 75 μL of XL-1 Blue Ultracompetent cells as per manufacturers directions. Transformants were screened by resistance to digestion with PmlI. The deletion was verified by dideoxy chain terminator sequencing using an internal IFN-τ primer identical to bases 312–335 of the non-coding strand.

Once the mutations were verified by sequencing, the plasmid DNA was transformed into *Pichia pastors*. Successful transformations were obtained with four of the mutants: 13E→R yielded 4 transformants, 16K→M yielded 5 transformants, 26P→L yielded 3 transformants, and 34K→H yielded 9 transformants.

changes were synthesized by Bioserve (Laurel, Md.) or Integrated DNA Technologies (Coralville, Iowa). They were added to 50–100 ng of pPICZα containing the gene for ovIFN-τ1mod with Pfu turbo polymerase (Stratagene) in a 50 μl reaction and cycled to incorporate the desired base change(s). Each reaction was optimized for each set of primers. Five μl of the PCR reaction was run on a 1% agarose gel to visualize the product. The remaining reaction was digested with Dpn 1 for 1 hour, purified, and used to transform XL-1 Blue Ultracompetent cells (Stratagene). Transforments were selected on low salt LB in the presence of zeocin (Invitrogen). Plasmid DNA from transformants was extracted with phenol-chloroform and ethanol precipitated. The incorporation of the correct mutations was verified by dideoxy sequencing.

Details:

The primers used were as follows:

TABLE 1

| Sample | Coding Strand | Non-Coding Strand |
|---|---|---|
| 13E→R | 5'-GCGACTGATGCTGGACGCTCGAGGTA ATTTAAAACTGCTGGACCG-3' | 5'-CGGTCCAGCAGTTTTAAATTACCTCGAGCG TCCAGCATCAGTCGC-3' |
| 16K→M | 5'-GCTGGACGCTCGAGAAAATTTAATGCT GCTGGACCGTATGAATCG-3' | 5'-CGATTCATACGGTCCAGCAGCATTAAATTT TCTCGAGCGTCCAGC-3' |
| 19D→A | 5'-CGAGAAAATTTAAAACTGCTGGCCCGT ATGAATCGATTGTCTCCGCAC-3' | 5'-GTGCGGAGACAATCGATTCATACGGGCCA GCAGTTTTAAATTTTCTCG-3' |
| 24L→I | 5'-CTGCTGGACCGTATGAATCGAATTTCT CCGCACAGCTGCCTGC-3' | 5'-GCAGGCAGCTGTGCGGAGAAATTCGATTC ATACGGTCCAGCAG-3' |
| 26P→L | 5'-CCGTATGAATCGATTGTCTCTGCACAG CTGCCTGCAAGACCGG-3' | 5'-CCGGTCTTGCAGGCAGCTGTGCAGAGACA ATCGATTCATACGG-3' |
| 34K→H | 5'-CTGCCTGCAAGACCGGCACGACTTCG GTCTGCCG-3' | 5'-CGGCAGACCGAAGTCGTGCCGGTCTTGCA GGCAG-3' |

Mutations are Indicated by Underlining

The PCR reaction was optimized for each pair of primers. For example, the optimal reaction conditions for each set of primers are summarized below.

TABLE 2

| Sample | Template | Primer (each) | dNTP | Annealing Temp. | Annealing Time | Extension Temp | Extension Time |
|---|---|---|---|---|---|---|---|
| 13E → R | 200 ng | .25 ng | 10 mM | 65° C. | 45 s | 72° C. | 8.5 min |
| 16K → M | 400 ng | .25 ng | 10 mM | 65° C. | 45 s | 72° C. | 8.5 min |
| 19D → A | — | — | — | — | — | — | — |
| 20R → Q* | 100 ng | .25 ng | 10 mM | 55° C. | 45 s | 68° C. | 10 min |
| 24L → I | 400 ng | .25 ng | 10 mM | 65° C. | 45 s | 72° C. | 8.5 min |
| 26P → L | 250 ng | .25 ng | 10 mM | 72° C. | 45 s | 72° C. | 8.5 min |
| 34K → H | 400 ng | .25 ng | 10 mM | 65° C. | 45 s | 72° C. | 8.5 min |

Site Directed Mutagenesis

Six nucleic acid mutations were introduced into ovine IFN-tau1mod DNA using the Quickchange Site Directed Mutagenesis kit (Stratagene) following manufacturers instructions. Briefly, primers containing the desired base These reactions were repeated for a total of 25 cycles. The strand dissociation temperature was 94° C. for 30 seconds, after cycling, each reaction was kept at 4° C.

Part (5 μL) of the PCR reaction was analyzed by agarose gel electrophoresis and if product was visualized, it was then digested with 12 units of DpnI for a minimum of 2 hours. The digestion was purified using GENECLEAN® and resuspended in 6 µL of TE, all of which was transformed into XL-1 Blue Ultracompetent cells (75 µL). Transformants were selected on low salt LB plates containing zeocin. Plasmid DNA was prepared on a "miniprep" scale and was phenol-chloroform purified (Maniatis) for sequencing. The sequencing primer was the alpha factor primer (Invitrogen), which is complementary to part of the non-coding strand of the sequence directly upstream of the IFN-τ gene in pPICZα. The sequencing primer has the following nucleic acid sequence:

5'-TACTATTGCCAGCATTGCTGC-3'

Production of Mutant IFN-τ Proteins in *P. pastoris*-*E. coli* carrying the recombinant plasmid was cultured overnight in low salt LB with zeocin and the plasmid DNA extracted. Plasmid DNA was linearized by digestion with Sac I overnight, purified, and resuspended in 5–10 µl of water. This DNA was used to transform *P. pastors* either by electroporation or chemically by using the Pichia EasyComp kit (Invitrogen). 100 µl of the yeast transformation mix was plated on YPD (1% yeast extract, 2% peptone, 2% dextrose) plates containing zeocin and incubated at 30° C. for 3 days to allow selection of yeast containing the desired gene. Individual colonies were selected and grown in 25 ml of BMGY media (1% yeast extract, 2% peptone, 100 mM potassium phosphate, pH 6.0, 1.34% yeast nitrogen base, $4 \times 10^{-5}$% biotin, 1% glycerol). For production of mutant proteins, cultures were shaken vigorously at 30° C. in the presence of light to an $OD_{600}$ of 2–6. They were harvested by centrifugation at 2500×g for 5 min, the pellet resuspended in BMMY media (1% yeast extract, 2% peptone, 100 mM potassium phosphate, pH 6.0, 1.34% yeast nitrogen base, $4 \times 10^{-5}$% biotin, 1% methanol) and again shaken vigorously at 30° C. for 1–2 days to induce the expression of the proteins. Proteins were secreted into the media and purified by ammonium sulfate precipitation and anion exchange column chromatography. The concentration of IFN-τ and mutant IFN-τ proteins was measured using the BCA protein assay (Pierce). The protocol was optimized for low concentrations of protein using an incubation period of 60° C. for 30 min.

Details:

Transformation Into Yeast:

Once the mutation had been verified by sequencing, plasmid DNA was prepared on a miniprep scale using Matrix (Biol101), three minipreps for each sample. The plasmid was linearized using SacI (Stratagene). Over 60 units of enzyme was needed to cut approximately 5 µg of DNA in 270 µL. This reaction was allowed to proceed overnight. About 10 µL of the reaction was then analyzed by agarose gel electrophoresis to ensure the digestion was successful. The rest of the reaction was purified by GENECLEAN®, resulting in a decrease in volume to 10 µl. All 10 µL were added to electrocompetent *Pichia pastoris*. Yeast were made competent by a modified protocol from Invitrogen; specifically, the $OD_{600}$ was allowed to reach 2–3 instead of 1.3–1.5 and the cells were allowed to recover without antibiotic selection for 6 hours before plating on YPD plates with sorbitol and zeocin (Pichia expression kit, Invitrogen). The electroporation was performed using an *E. coli* pulser (Biorad). The cells were pulsed with 180 kV for 10 milliseconds in a 0.2 cm cuvette. Ice-cold (1 mL, 1 M) sorbitol was added to the cells as they recovered before plating.

Screening for Mutant IFN Production

Individual cultures of each of the transformants were grown in BMGY media (25 mL). After 2 days of growth with vigorous shaking at 30° C. in the presence of light, the cultures were centrifuged at 2500×g for 5 minutes. The pellet was resuspended in BMMY medium (25 mL) to induce IFN production. IFN-τ is secreted by yeast strain Pichia pastoris. After 1 to 3 days, a sample of the media was analyzed on a 15% non-denaturing polyacrylamide gel to look for the presence of a 19 kD protein. If such a protein was present, a chemiluminescent western blot was performed (Amersham). The blot was visualized using rabbit anti-IFN antibodies (HL-98) as the primary antibody and mouse anti-rabbit linked to alkaline phosphatase as the secondary antibody. Detection was sensitive to 50 ng of protein. If mutant IFN was found to be present, the culture was centrifuged at 10,000×g for 5 minutes and the supernatant was removed.

Purification of Mutant IFN

The media containing mutant IFN was then stirred overnight at 4° C. in an equal volume of saturated ammonium sulfate (Harlowe, 1988) to precipitate proteins. The ammonium sulfate-IFN mixture was then centrifuged at 2500×g for 30 minutes. The pellet was then resuspended in 10 mM Tris pH 7.5. The protein was then loaded onto a DEAE (Whatman) ion exchange column. A gradient was made from 10 mM Tris pH 7.5 with no salt to 500 mM NaCl in 600 mL. As the salt concentration increased, the protein was eluted, and eluant was collected in 3 mL aliquots. Each aliquot was then tested by spectrophotometry for absorbance at 280 nm. The fractions with high absorbances were pooled and concentrated. The concentrated protein solution was then visualized on a 15% non-denaturing polyacrylamide gel to gauge purity. If it was deemed pure, the protein was sterile filtered and frozen in 200 μL aliquots at −80° C. One aliquot was kept at −20° C. for assay purposes.

The protein can be purified by standard methods, including size fractionation (column chromatography or preoperative gel electrophoresis) or affinity chromatography (using, for example, anti-Ovine IFN-tau. antibodies (solid support available from Pharmacia, Piscataway N.J.). Protein preparations can also be concentrated by, for example, filtration (Amicon, Danvers, Mass.). The amount of r-IFN-tau. can be quantified using standard assays known in the art including radioimmunoassay and Elisa, and bioassays known to those skilled in the art.

Protein Assay

The concentration of IFN was measured by the BCA protein assay kit (Pierce). The absorbance was read at 560 nM and compared to a bovine serum albumin (BSA) standards ranging from 20 μg/mL to 120 μg/mL. The protocol was optimized for low concentrations of protein using an incubation period of 30 minutes at 60° C.

Structural Determinations-Circular Dichroism (CD) of the IFN-τ mutants was determined at room temperature with a JASCO 500C spectropolarimeter. Scans were done with a 0.1 mm pathlength cell at a sensitivity of 2 and a time constant of 8 sec. The wavelength range measured was from 250 nm to 184–188 nm at a scan rate of 20 nm/min. Scans were carried out on IFN-τ mutants in water at 0.16–0.5 mg/ml. The CD spectra were expressed in terms of ellipticity, θ, related to the means residue molecular weight for each IFN-τ mutant. The following formula was used to generate θ (Yang): Mean residue ellipticity $[\theta]=100\times[\theta]_{observed}/c\times l$, where $[\theta]_{observed}$ is expressed in degrees, c equals the mean residue concentration in mol/liter, and l is the pathlength of the cell in cm.

Ovine IFN-τ1mod Mutant Protein Immunoblots-Purified proteins were run on a 15% polyacrylamide gel and transferred to Hybond membrane (Amersham, Piscataway, N.J.).

Membranes were incubated with a 1:500 dilution of the monoclonal antibody HL-98 made against a C-terminal region peptide of ovIFN-τ1mod. Recognition of both native and denatured ovIFN-τ1mod by this antibody is not dependent on a conformational determinant (20). The secondary antibody was peroxidase-conjugated sheep anti-mouse antibody. The proteins were detected using ECL according to the manufacturers instructions (Amersham). A single band at 19 KD was visualized in each lane. One mutant IFN-tau protein was run in each lane. Therefore this result confirms that the molecular weight of the tau mutants is exactly the same as native ovine IFN-tau.

Competitive Binding of ovine IFN-□ to Receptors on MDBK Cells-OvIFN-tau1mod was labeled with the Bolton-Hunter reagent (mono [$^{125}$I] iodo derivative, 2,000 Ci/mmol, Amersham; 1 Ci=37 GBq) as previously described (8). Specific activity of the labeled protein was ~20 pCi/□g. The labeled ovIFN-tau1mod retained complete antiviral activity on MDBK cells. For binding, 3 nM of $^{125}$I-ovIFN-tau1mod were incubated with 7.5×10$^5$ MDBK cells in the absence or presence of 300 nM unlabeled ovIFN-tau1mod, IFN-alphaA or IFN-tau mutants in 500 microlitersl of MEM/10% FBS at 4° C. for 12–14 h (21). The cells were layered over 10% (w/v) sucrose in PBS (2.5 ml), centrifuged at 12,000×g for 30 min at 4° C., and the pellets counted. Specific binding was defined as total binding minus nonspecific binding in the presence of a 100 fold molar excess of unlabeled IFN-alpha A.

Antiviral Assay Antiviral activity is measured using a standard cytopathic effect inhibition assay using MDBK cells and vesicular stomatitis virus (VSV; 22). Antiviral activity was normalized based on the reference IFN-alpha Gxa01-901-535.

Details:

Madin Darby Bovine Kidney (MDBK) cells (ATCC). MDBK cells were plated on a polystyrene coated 96-well plate at a concentration of 6×10$^5$ cells/mL and grown overnight at 37° C. in 5% $CO_2$/95% air. The cells were then visualized under 40× magnification to ensure confluency. The media was removed and the replaced with MEM supplemented with 2% FBS and serial dilutions of IFN. Each IFN was assayed in duplicate. The lowest dilution was 1:10 and the rest of the plate consisted of 1:3 serial dilutions. One column received only medium, as a control. The first assay for each IFN was performed as described above. If the IFN had a high activity or a high concentration of protein, it was diluted 1:100 for the initial dilution. The serial dilutions were always 1:3. The cells were incubated with IFN for 24 hours at 37° C. in 5% $CO_2$/95% air.

The cells were then challenged with a 1:500 dilution of Vesicular Stomatitis Virus (VSV) in MEM, supplemented with 2% FBS. Four of the control wells received only medium and four of the control wells received medium plus virus. Each of the IFN-treated wells received medium plus virus. The cells were incubated with virus for another 24 hours at 37° C. in 5% $CO_2$/95% air. The cells were then stained with crystal violet (100 µL; 0.5% in 30% methanol; Sigma) for 5 minutes and washed with distilled water. One antiviral unit was defined as the concentration of IFN at which 50% destruction of the monolayer was observed.

Antiproliferative Activity

Antiproliferative activity was measured on two adherent cell lines, MCF-7 (breast adenocarcinoma) and HT-29 (colon adenocarcinoma), and one suspension cell line, Daudi (Burkitt lymphoma). For the adherent cell lines, 1000 cells/ml were plated in a 24 well polysterene plate. 10,000 units of ovine IFN-tau1mod was added, or the equivalent molar concentration (17 nM) of IFN-alphaA (32,000 U/ml–10,000 U/ml was used in a set of 3 replicate experiments with no difference in effect), or IFN-tau mutants. Cells were incubated at 37° C. in 5% $CO_2$ for 9 days. Cells were detached with 0.25% trypsin and counted using a hemocytometer. Viability was determined by trypan blue staining. For Daudi cells, 1000 cells/ml were incubated with 33 units of IFN-tau or the equivalent concentration (0.06 nM) of IFNalpha□, or IFN-tau mutants in 5 ml polypropylene tubes. Cells were incubated at 37° C. in $CO_2$ for 3–4 days, centrifuged for 5 minutes at 300×g, and the pellet resuspended in 1% trypan blue in phosphate buffered saline and counted.

Cytotoxicity Assay—80,000 U/ml of either ovine IFN-tau1mod, IFN-alphaA or IFN-tau mutants were added to 2×10$^5$ U937 cells in polypropylene tubes in triplicate and incubated for 72 hours. Control cells were treated with medium alone. Cells were counted with a hemocytometer after the addition of trypan blue.

Statistical Analysis-Statistically significant differences ($p<0.05$) between experimental means were determined by analysis of variance followed by Least Significant Difference.

EXAMPLE II

Identification of Six Interferon Tau 1Mod Mutants

Six mutants of IFN-tau1mod have been constructed. It was decided to select for substitution, those amino acids in the N terminal region of native ovine IFN-tau that are exposed to solvent AND that differ from the corresponding solvent-exposed amino acid on human Interferon alpha. Those amino acids in the N-terminal region of each molecule that are exposed to solvent were identified based on IFN-tau's crystallographic structure. If the crystal structure is unknown, the solvent-exposed amino acids could be predicted from the molecular data about the protein. The amino acids exposed to solvent were compared and the amino acids in this group that were different between interferon tau and alpha were identified. Six mutations were made in interferon tau, one amino acid at a time, chosen from the solvent-exposed amino acids that were different between IFN-tau and IFN-alpha. The mutations were created using site directed mutagenesis to specifically convert one specific amino acid in ovine IFN-τ1mod to the amino at the corresponding position in human IFN-alphaA by changing the DNA codon. Other methods of making the appropriate DNA for the tau mutants known to those skilled in the art can be used. Three mutations were at sites within helix A and three within the AB loop where the solvent exposed amino acid sequence of ovine IFN-τ1mod was shown to differ from to the amino acid at the corresponding position in human IFN-alphaA These six solvent-exposed amino acids in IFN-τ were substituted with the corresponding differing amino acid found in IFN-α. The nine amino acids that are different between IFN-α and IFN-τ and are exposed to solvent are indicated below by bold and underlining. Even though Residue 34 was not exposed to solvent, this residue is recognized in the art as being significant for biological activity therefore the 34 K:H substitution indicated below was made. Six of these differing amino acids were targeted for mutation.

```
                1         10        20        30
IFN-τ    CYLSRKLMLDARENLRLLDRMNRLSPHSCLQDRKDF

IFN-α    CDLPQTHSLGSRRTLMLLAQMRKISLFSCLKDRHDF
```

Differences between -τ and -α are in bold. Solvent-exposed residues are underlined.
The six mutations are as follows:

TABLE 3

| Sample | Residue # | Old A.A. | New A.A. | Old Codon | New Codon | Region |
|---|---|---|---|---|---|---|
| 5R → Q | 5 | Arg | Gln | CGA | Not done | N terminus |
| 6K → T | 6 | Lys | Thr | AAA | Not done | " |
| 13E → R | 13 | Glu | Arg | GAA | CGT | " |
| 16K → M | 16 | Lys | Met | AAA | ATG | " |
| 19D → A | 19 | Asp | Ala | GAC | GCC | " |
| 20R → Q | 20 | Arg | Gln | CGT | Not done | " |
| 24L → I | 24 | Leu | Ile | TTG | ATT | AB Loop |
| 26P → L | 26 | Pro | Leu | CCG | CTG | " |
| 31Q → K | 31 | Gln | Lys | CAA | AAG | " |
| 34K → H | 34 | Lys | His | AAA | CAC | " |

The mutations identified by their amino acid sequence, and one possible nucleic acid sequence are:
The mutations identified by their amino acid sequences are:

| | |
|---|---|
| THE 13 E:R MUTANT | AMMINO ACID SEQ. ID NO. 4, NUCLEIC ACID SEQ. ID NO. 11, |
| THE 16 K:M MUTANT, | AMMINO ACID SEQ. ID NO. 5, NUCLEIC ACID SEQ. ID NO. 12 |
| THE 19 D:A MUTANT | AMMINO ACID SEQ. ID NO. 6, NUCLEIC ACID SEQ. ID NO. 13, |
| THE 24 L:I MUTANT | AMINO ACID SEQ. ID NO. 7; NUCLEIC ACID SEQ. ID NO. 14 |
| THE 26 P:L MUTANT | AMINO ACID SEQ. ID NO. 8, NUCLEIC ACID SEQ. ID NO. 15; |
| THE 31 Q:K MUTANT | AMINO ACID SEQ. ID NO. 9, NUCLEIC ACID SEQ. ID NO. 16; |
| THE 34 K:H MUTANT | AMINO ACID SEQ. ID NO. 1O, NUCLEIC ACID SEQ. ID NO. 17 |
| THE 5 R:Q MUTANT | AMINO ACID SEQ. ID NO. 18, |
| THE 6 K:T MUTANT | AMINO ACID SEQ. ID NO. 19, and |
| THE 20 R:Q MUTANT | AMINO ACID SEQ. ID NO. 20. |

It is important to emphasize that due to redundancy in the genetic code, the nucleic acid sequences set forth above are only one of many nucleic acid sequences for each respective mutant. Other IFN-tau mutants that were identified but not made are 5 R:Q which has the same amino acid sequence as native ovine IFN-tau1mod in SEQ. ID No. 2, except for having a glycine (GLN) residue instead of an arginine (ARG) at position 5; 6 K:T which has the same amino acid sequence as native ovine IFN-tau1mod in SEQ. ID No. 2, except for having a threonine residue instead of a lysine at position 6; and 20 R:Q which has the same amino acid sequence as native ovine IFN-tau1mod in SEQ. ID No. 2, except for having a glycine residue instead of an arginine at position 20. The 5, 6 and 20 IFN-tau mutants also come within the present invention.

The recombinant IFN-τ containing each mutation was expressed and purified AS DESCRIBED ABOVE. All mutant IFN-tau proteins were recognized by an anti C-terminal monoclonal antibody against IFN-tau1mod in immunoblots. Only the 13 E:R mutation decreased alpha-helical content as assessed by Circular Dichroism (data not shown).

EXAMPLE III

Binding of the Mutant Interferon Tau proteins to the Type I IFN Receptor-Binding of $^{125}$I-ovIFN-τ1Mod to the Common Type I IFN Receptor Binding of the mutant interferon tau proteins to the Type I IFN Receptor-Binding of $^{125}$I-ovIFN-τ1mod to the common type I IFN receptor was most efficiently displaced by human IFN-alphaA (FIG. 1). OvIFN-τ1mod itself produced only half of the displacement seen with the IFNτ. The majority of the amino acid substitutions introduced decreased the ability of the mutant proteins to displace the labeled ovIFN-τ1mod from the receptor; however, this decrease was significant with the 24L:I and 34K:H mutants. However, the P:L substitution at residue 26 significantly increased competition of labeled ovIFN-τ1mod binding, though still not to the same extent as did the human IFN-alphaA.

The potency of various IFNs has been suggested to be related to receptor binding affinity (25). The reduced antiproliferative potency and reduced toxicity of ovIFN-τ1mod relative to human IFN-τ on MDBK cells has been seen as a reflection of Kd, $3.90 \times 10^{-10}$ and $4.45 \times 10^{-11}$ for IFN-τ and α, respectively (8). Hence, the enhanced receptor binding of the IFN-τ 26 P:L mutant relative to the parental IFN-τ can be predictive of enhanced BIOLOGICAL ACTIVITY OR potency.

EXAMPLE IV

Antiprolifetativ Activity of Interferon Tau Mutants

The ability of IFNs to decrease cell proliferation is a well documented phenomenon. The results set forth below show that the N-terminal substitutions had cell type-specific effects on antiproliferative activity, but each of the mutants maintained equivalent antiproliferative activity relative to the parental IFN-τ on at least one cell line. Antiproliferative activity was measured on two adherent cell lines, MCF-7 (breast adenocarcinoma) and HT-29 (colon adenocarcinoma), and one suspension cell line, Daudi (Burkitt lymphoma). Antiproliferative activity is measured as the percent of cells grown in the presence of IFN divided by the number of cells grown in the absence of IFN.

Daudi Cells (Burkitt Lymphoma).

We first evaluated the antiproliferative activities of the various IFN-τ mutants on Daudi cells at a concentration equivalent to that which caused marked inhibition of cells when treated with IFN-τ. Thirty-three units of ovIFN-1mod (0.06 nM) caused a 54% decrease in Daudi cell proliferation (Table 1). The same concentration of human IFN-alphaA caused an even greater decrease in proliferation of 69%. All of the mutants tested reduced the cell numbers as well as, or better, than ovIFN-τ1mod. The 26P:L mutant exhibited the greatest antiproliferative activity against Daudi cells. This mutant caused an 81% decrease in cell number as compared to cells in media alone, an activity profile better than human IFN-alphaA. Thus, the 26P:L mutant has both the highest level of antiviral activity, and the highest activity at inhibiting proliferation of Daudi cells.

16 K:M and 34K:H mutants are also clinically significant as antiproliferative agents in the treatment of cancer, because both were nearly as effective as IFNα without the toxicity, and both were more effective than interferon-tau. This means that the 26, 16, and 34 mutants described above all have significantly better therapeutic indices than human IFN-alpha A and native ovine IFN-tau for treating cancer and tumors.

MCF-7 (Breast Adenocarcinoma) and HT-29 (Colon Adenocarcinoma)

HT-29 and MCF-7 were also used to test the antiproliferative activity of the interferon-tau mutants. These cell lines are not as sensitive to type I IFNs as are Daudi cells and they therefore required much higher doses to inhibit cell growth. 10,000 units (17 nM) of ovIFN-tau1mod added to HT-29 cells caused a 44% decrease in cell number compared to control ($1.61 \times 10^6$ c/ml versus $2.85 \times 10^6$ c/ml). 10,000 units (17 nM) of ovIFN-tau1mod added to MCF-7 cells caused a 54% decrease in cell number compared to controls.

Five of the six IFN-tau mutants significantly decreased cell number of both HT-29 and MCF-7 cells compared to control when given at 17 Nm. For HT-29 cells, only the 24 L:I mutant failed to show an increase in antiproliferative activity, despite the fact that this mutation is conservative. The 26 P:L mutation had significantly increased antiproliferative activity (cell growth decreased 63% relative to controls) while wildtype IFN-τ showed less antiproliferative activity (cell growth decreased 44% relative to controls).

All of the mutants inhibited proliferation of MCF-7 cells compared to controls when used at 17 nM; however, the antiproliferative activity of the mutants (62–90%) did not significantly differ from that of ovine IFN-τ1mod (86%). Again the IFN-τ 26P:L mutant had the greatest antiproliferative activity (90%), although it was not significantly different from either parental ovine IFN-τ1mod or human IFN-αA.

TABLE 4

Antiproliferative Activity of IFN-tau N-terminal mutants.*

| Treatment | HT-29 Cells | Daudi Cells | MCF-7 Cells |
|---|---|---|---|
| Control | 285 ± 19 | 34.1 ± 2.1 | 130 ± 17 |
| IFN-αA | 62 ± 4(78%) | 10.6 ± 0.2(69%) | 2 ± 2(99%) |
| Ovine IFN-τ1mod | 161 ± 6(44%) | 15.9 ± 1.2(54%) | 18 ± 8(86%) |
| IFN-τ13 E:R | 175 ± 27(39%) | 14.8 ± 1.3(57%) | 38 ± 7(71%) |
| IFN-τ16 K:M | 117 ± 27(39%) | 9.4 ± 0.5(72%)† | 50 ± 9(62%) |
| IFN-τ19 D:A | 141 ± 32(51%) | ND | 25 ± 6(80%) |
| IFN-τ24 L:I | 237 ± 86(17%) | ND | 39 ± 6(70%) |
| IFN-τ26 P:L | 104 ± 13(63%)† | 6.2 ± 0.4(81%)† | 13 ± 7(90%) |
| IFN-τ34 K:H | 137 ± 35(52%) | 10.7 ± 1.1(69%)† | 37 ± 8(72%) |

*17 nM of each IFN was added to 1000 MCF-7 or HT-29 cells and incubated for 9 days. 0.06 nM of each IFN was added to 1000 Daudi cells and incubated for 3 days. Control cultures received no IFN. Results are expressed as the mean cell numer x $10^4$ ± SE of three replicate experiments. Percent inhibition is indicated in parentheses. ND indicates not done. A "†" indicates a significant increase in growth inhibition by the IFN-τ mutants relative to that of ovine IFN-τ 1mod.

EXAMPLE V

Toxicity of the Interferon Tau Mutants
Viability of IFN-tau Mutant-Treated Cells 80,000 U/ml of either ovine IFN-tau1mod, IFN-alphaA or IFN-tau mutants was added to $2 \times 10^5$ U937 cells in polypropylene tubes in triplicate and incubated for 72 hours. Control cells were treated with medium alone. Cells were counted with a hemocytometer after the addition of trypan blue.

As with peripheral blood lymphocytes, U937 cells exhibit significantly reduced viability when treated with human IFN-alphaA: viability in controls is about 97.5% and in IFN-alphaA treated cells it is about 83%. By contrast viability in cells treated with native ovine IFN-tau 1mod is about 96%. All of the IFN-tau mutant proteins showed very high viability and essentially no cytotoxicity. In a first viability study, percent viability was: 94.75% for the 13 E:R mutant; 97.25% for the 16 K:M mutant; 95.75% for the 26 P:L mutant; and 95.5% for the 34 K:H mutant. See Table 5. In a second viability study which also included the 19D:A mutant and the 24 L:I mutant, % viability was: control 98.9%; native IFN-tau 97%; human IFN-alpha 80.25%; 96% for the 13 E:R mutant; 97% for the 16 K:M mutant; 97% for the 19D:A mutant; and 96.5% for the 24L:I mutant. See Table 6.

TABLE 5

VIABILITY OF U937 CELLS

| Source: | df: | Sum of Squares: | Mean Square: | F-test: | P-value: |
|---|---|---|---|---|---|
| Between subjects | 3 | 21.632 | 7.211 | .205 | .8922 |
| Within subjects | 24 | 845.696 | 35.237 | | |
| treatments | 6 | 634.031 | 105.672 | 8.986 | .0001 |
| residual | 18 | 211.665 | 11.759 | | |
| Total | 27 | 867.328 | | | |

Reliability Estimates for- All treatments: –3.887 Single Treatment: –.128

One Factor ANOVA-Repeated Measures for $X_1 \ldots X_7$

| Group: | Count: | Mean: | Std. Dev.: | Std. Error: |
|---|---|---|---|---|
| media | 4 | 97.562 | 1.638 | .819 |
| ifnt | 4 | 95.75 | 2.5 | 1.25 |
| ifna | 4 | 82.75 | 7.194 | 3.597 |
| 13E:R | 4 | 94.75 | 2.872 | 1.436 |
| 16K:M | 4 | 97.25 | 1.5 | .75 |

One Factor ANOVA-Repeated Measures for $X_1 \ldots X_7$

| Group: | Count: | Mean: | Std. Dev.: | Std. Error: |
|---|---|---|---|---|
| 26P:L | 4 | 95.75 | 2.217 | 1.109 |
| 34K:H | 4 | 95.5 | 1.291 | .645 |

TABLE 6

VIABILITY OF U937 CELLS

| Source: | df: | Sum of Squares: | Mean Square: | F-test: | P-value: |
|---|---|---|---|---|---|
| Between subjects | 1 | 14.535 | 14.535 | .312 | .5854 |
| Within subjects | 14 | 652.586 | 46.613 | | |
| treatments | 7 | 499.965 | 71.424 | 3.276 | .0701 |
| residual | 7 | 152.621 | 21.803 | | |
| Total | 15 | 667.121 | | | |

Reliability Estimates for- All treatments: –2.207 Single Treatment: –.094

One Factor ANOVA-Repeated Measures for $X_1 \ldots X_8$

| Group: | Count: | Mean: | Std. Dev.: | Std. Error: |
|---|---|---|---|---|
| media | 2 | 98.875 | .177 | .125 |
| ifnt | 2 | 97 | 0 | 0 |
| ifna | 2 | 80.25 | 10.96 | 7.75 |

TABLE 6-continued

VIABILITY OF U937 CELLS

| 13 E:R | 2 | 96 | 4.243 | 3 |
| 16 K:M | 2 | 97 | 1.414 | 1 |

One Factor ANOVA-Repeated Measures for $X_1 \ldots X_8$

| Group: | Count: | Mean: | Std. Dev.: | Std. Error: |
|---|---|---|---|---|
| 19 D:A | 2 | 97 | 1.414 | 1 |
| 24 L:I | 2 | 96.5 | 3.536 | 2.5 |
| 26 P:L | 2 | 96.5 | 3.536 | 2.5 |

EXAMPLE VI

Antiviral Activity

IFNs have historically been described by their antiviral activity, so this was a logical screen for the activity of the IFN-τ mutants. The ability of the six mutants to protect MDBK cells against VSV was tested and their antiviral activities were compared to that of wildtype ovIFN-τ1mod and human IFN-αA. One unit of antiviral activity is defined as the amount of protein needed to inhibit the cytopathic effect of VSV by 50%.

All the mutants possessed antiviral activity to some extent. The activity of the IFN-tau 26P:L mutant was 9.5× $10^7$ U/mg, which is as great as that of both ovine IFN-tau and human IFN-alphaA. This is especially significant because the 26P:L mutation provides an interferon tau mutant that has antiviral activity equivalent to that of both ovine IFN-tau and human IFN alpha, with antiproliferative activity that is much increased over native IFN tau (see below) and low toxicity. The clinical significance is that this mutant has a much better therapeutic index than human IFN alpha.

The activity of four other mutants, 16K:M, 19D:A, 24L:I, and 34K:H, exhibited significantly reduced the antiviral activity relative to the parental IFN controls. The least active mutant was 13E:R, having 3.2×$10^4$ units of activity/mg protein. This is significantly less antiviral activity than wildtype ovIFN-τ1mod (6.4×$10^7$ U/mg) or IFN-alpha (8×$10^7$ U/mg). The reduced antiviral activity of 13 E:R did not correlate with receptor binding, since binding of 13 E:R was equivalent to that of ovIFN-tau1mod. The antiviral activities of the various mutants are summarized below.

It should be emphasized that antiviral activity against bovine MDBK cells was tested because this is a recognized method to screen for interferons. A high level of antiviral activity in this assay does not necessarily correlate with exceptionally good antiviral activity in humans, nor is the reverse necessarily true. Antiviral activity like antiproliferative activity, is anticipated to be viral- and host-specific. One discovery and embodiment of this invention is using specific cell lines and viruses to assess bioactivity and creating optimal drugs for each virus/host combination. The optimal drug may be dependent on the host HLA or other immunotype.

TABLE 7

ANTIVIRAL ACTIVITY OF INTERFERON TAU MUTANTS

| Sample | Average (U/mg) | Standard Deviation |
|---|---|---|
| IFN-α | 8.8 × $10^7$ | — |
| IFN-τ | 6.9 × $10^7$ | 6.0 × $10^7$ |
| 13E → R | 3.2 × $10^4$ | 2.3 × $10^4$ |
| 16K → M | 1.9 × $10^5$ | 1.2 × $10^5$ |
| 19 D:A | 1.3 × $10^6$ | 5.4 × $10^5$ |
| 24 L:I | 3.3 × $10^6$ | 1.5 × $10^5$ |
| 26P → L | 9.5 × $10^7$ | 8.9 × $10^7$ |
| 34K → H | 2.5 × $10^6$ | 2.4 × $10^6$ |

Table 7—Antiviral Activity of IFN mutants on MDBK cells. Antiviral activity was measured using serial dilutions of IFN from 1:100 to 1:5.9×$10^7$ Challenge was with a 1:500 dilution of stock VSV. Averages are based on 2–15 replicates. ANOVA was based on 5 replicates.

All documents cited above are hereby incorporated in their entirety by reference. The entire contents of U.S. Provisional Appln. 60/140,411, filed Jun. 22, 1999, is incorporated herein by reference.

One skilled in the art will appreciate from a reading of this disclosure that various changes in form and detail can be made without departing from the true scope of the invention.

What is claimed is:

1. A method for making a recombinant protein having improved biological activity comprising (i) selecting tau 1mod of SEQ ID NO. 2 as a first protein for which biological activity is to be improved, (ii) identifying a second protein that is structurally similar to the first protein, which second protein has the desired biological activity and for which the amino acid sequence is known, (iii) identifying one or more amino acids on said first protein that are different from the corresponding amino acids on the second protein, and (iv) substituting one or more of the differing amino acids identified in the second protein in (iii), for the corresponding one or more amino acids in the first protein, to obtain the recombinant protein having the improved biological activity.

2. A method of claim 1, wherein step (iv) comprises making one or more mutations to the nucleic acid sequence of the first protein to make a recombinant nucleic acid sequence that includes codons for the one or more substituted amino acids, and then translating the recombinant nucleic acid sequence in vivo or in vitro to obtain the recombinant protein having improved biological activity.

3. The method of claim 1, wherein the second protein is interferon alpha.

4. The method of claim 3, wherein the interferon alpha is human interferon alphaA identified by amino acid SEQ. ID NO. 3.

5. The method of claim 1, wherein the biological activity is antiviral activity.

6. The method of claim 5, wherein the antiviral activity inhibits viral replication.

7. The method of claim 1, wherein the biological activity is antiproliferative activity.

8. The method of claim 1, wherein the one or more differing amino acids are located in a binding site or other region of known biological activity.

9. The method of claim 1, wherein step (iii) comprises:
a)-determining which amino acids in the first protein are exposed to solvent,
b)-determining which amino acids in the second protein are exposed to solvent,
c)-determining which solvent-exposed amino acids on the second protein are different form the corresponding solvent-exposed amino acids on the native protein.

10. The method of claim 1, wherein the first and second proteins are from the same species.

11. The method of claim 1, wherein the first and second proteins are from different species.

12. The method of claim 1, wherein the first and second proteins are naturally occurring proteins.

* * * * *